United States Patent
Sun et al.

(10) Patent No.: US 11,730,378 B2
(45) Date of Patent: Aug. 22, 2023

(54) HEART FAILURE MONITORING AND REDUCTION OF RESPIRATION INDUCED UNDER SENSING OF CARDIAC EVENTS

(71) Applicant: Pacesetter, Inc., Sylmar, CA (US)

(72) Inventors: Stephanie C. Sun, Camarillo, CA (US); Xiaoyi Min, Camarillo, CA (US); Alan B. Vogel, Saugus, CA (US); Fujian Qu, San Jose, CA (US); Stuart Rosenberg, Castaic, CA (US)

(73) Assignee: Pacesetter, Inc, Sylmar, CA (US)

( * ) Notice: Subject to any disclaimer, the term of this patent is extended or adjusted under 35 U.S.C. 154(b) by 379 days.

(21) Appl. No.: 17/229,898

(22) Filed: Apr. 14, 2021

(65) Prior Publication Data

US 2021/0228093 A1 Jul. 29, 2021

Related U.S. Application Data

(62) Division of application No. 15/803,596, filed on Nov. 3, 2017, now Pat. No. 11,000,189.

(51) Int. Cl.

| | |
|---|---|
| *A61B 5/0205* | (2006.01) |
| *A61B 5/00* | (2006.01) |
| *A61B 7/02* | (2006.01) |
| *A61B 7/04* | (2006.01) |
| *A61B 5/283* | (2021.01) |
| *A61B 5/024* | (2006.01) |

(Continued)

(52) U.S. Cl.
CPC ............ *A61B 5/0205* (2013.01); *A61B 5/283* (2021.01); *A61B 5/686* (2013.01); *A61B 5/6861* (2013.01); *A61B 5/7278* (2013.01); *A61B 5/7282* (2013.01); *A61B 7/023* (2013.01); *A61B 7/04* (2013.01); *A61B 5/0245* (2013.01); *A61B 5/02438* (2013.01); *A61B 5/0803* (2013.01); *A61B 5/1116* (2013.01); *A61B 5/1118* (2013.01); *A61B 5/725* (2013.01); *A61B 2562/0209* (2013.01); *A61B 2562/162* (2013.01)

(58) Field of Classification Search
CPC ....... A61B 5/0205; A61B 5/283; A61B 5/686; A61B 5/6861; A61B 5/7278; A61B 5/7282; A61B 5/02438; A61B 5/0245; A61B 5/1116; A61B 5/1118; A61B 5/725; A61B 2562/0209; A61B 2562/162
See application file for complete search history.

(56) References Cited

U.S. PATENT DOCUMENTS

| | | |
|---|---|---|
| 6,064,910 A | 5/2000 | Andersson et al. |
| 6,600,949 B1 | 7/2003 | Turcott |

(Continued)

*Primary Examiner* — Chu Chuan Liu
(74) *Attorney, Agent, or Firm* — The Small Patent Law Group LLC; Dean D. Small

(57) ABSTRACT

Computer implemented methods, systems and devices are provided to monitor for potential heart failure (HF). Cardiac activity (CA) data is obtained and filtered to obtain respiration data indicative of a respiration pattern. The respiration data is analyzed to determine one or more respiration characteristics of interest (COI) that are recorded along with collection time information to form an HF monitoring log. Additionally or alternatively, the CA data is analyzed to detect an event of interest. The cardiac activity data is filtered to obtain respiration data indicative of a respiration pattern, and the respiration data is analyzed for respiration induced under detection of the event of interest from the CA data.

25 Claims, 13 Drawing Sheets

(51) Int. Cl.
  *A61B 5/08* (2006.01)
  *A61B 5/11* (2006.01)
  *A61B 5/0245* (2006.01)

(56) References Cited

U.S. PATENT DOCUMENTS

| | | |
|---|---|---|
| 6,928,324 B2 | 8/2005 | Park et al. |
| 7,628,757 B1 | 12/2009 | Koh |
| 7,678,061 B2 | 3/2010 | Lee et al. |
| 9,022,030 B2 | 5/2015 | Turcott |
| 10,610,132 B2 | 4/2020 | Gunderson et al. |
| 2007/0213622 A1 | 9/2007 | Reisfeld |
| 2007/0233198 A1* | 10/2007 | Ghanem ............... A61B 5/364 607/5 |
| 2019/0111268 A1 | 4/2019 | Christie et al. |
| 2019/0133457 A1 | 5/2019 | Sun et al. |

* cited by examiner

HEART FAILURE MONITORING AND REDUCTION OF RESPIRATION INDUCED UNDER SENSING OF CARDIAC EVENTS

REFERENCE TO RELATED APPLICATIONS

The present application is a divisional application of, and claims priority to, U.S. application Ser. No. 15/803,596, Titled "HEART FAILURE MONITORING AND REDUCTION OF RESPIRATION INDUCED UNDER SENSING OF CARDIAC EVENTS" which was filed on 3 Nov. 2017, the complete subject matter of which is expressly incorporated herein by reference in its entirety.

FIELD OF THE INVENTION

Embodiments herein relate generally to implantable medical devices, and more particularly to implantable loop recorders for monitoring cardiac events such as heart rate and rhythm.

BACKGROUND OF THE INVENTION

Implantable cardiac monitors (ICM) is a small medical device that is implanted in a location to continuously monitor heart rhythms and record electrocardiograms (ECGs) automatically or with patient activation. An ICM uses electrodes placed at the distal and proximal end of the device to sense rhythms wirelessly at an orientation and location. The purpose of ICM is to help clinicians diagnose for, and treat, abnormal heart activities that can be either asymptomatic or cause symptoms such as seizures, recurrent palpitations (noticeably rapid, strong, or irregular heartbeats due to agitation, exertion, or illness), lightheadedness, dizziness, or syncope (fainting). These abnormal heart activities include bradycardia (slow heart rate), tachycardia (fast heart rate), asystole (no electrical heart activity), atrial or ventricular arrhythmias (problems with rate or rhythm of heart beat), and even atrial fibrillation (AF; very fast or irregular heart beat).

However, ICMs can exhibit false detection of cardiac arrhythmias under inappropriate R wave sensing. Several variables, like respiration, can cause the ICM to inappropriately detect heart signals such as by altering R-wave amplitudes and morphologies. For example, existing algorithms used by ICMs for detecting arrhythmias are primarily based on the irregularity of R-waves. The respiration signal modulates R-wave amplitudes. A breath occurs over a respiratory cycle that includes one inspiration phase (inhalation) and one expiration phase (exhalation). As a patient breathes, the chest expands and contracts, which causes the ICM to move relative to the heart. The lungs inflate and deflate, resulting in alternating increases and decreases in an amplitude of an ECG signal detected by the ICM. In other words, as lungs expand during inhalation, the ICM is pushed away from the heart. The change in heart-electrode distance results in a change in the signals measured by the electrodes at the ICM. In addition, the conductivity of lungs, when deflated, is about three times higher than when lungs are inflated, such that electric potentials that reach electrodes at the ICM also change during respiration. Patients have been observed to exhibit both an increase and decrease of R-wave amplitudes during a breathing test. The potential exists that the ICM detects heart beats simultaneous with the strong respiration artifact, thereby resulting in an inappropriate detection by the ICM. For example, the ICM may detect a normal heart rhythm as bradycardia or asystole, and/or the ICM may under-detect a tachycardia.

SUMMARY

In accordance with embodiments herein, a computer implemented method is provided to monitor for potential heart failure (HF). The method is under control of one or more processors that are configured with specific executable instructions. The method obtains cardiac activity data for multiple cardiac cycles, filters the cardiac activity data to obtain respiration data indicative of a respiration pattern over multiple respiration cycles, and analyzes the respiration data to determine one or more respiration characteristics of interest (COI). The method further records the respiration COI along with collection time information concerning when the CA data was obtained and repeats the operations at a) to d) to form an HF monitoring log that includes a collection of respiration COI over a period of time.

Optionally, the method determines a secondary index based on secondary data, the secondary data representing at least one of heart sounds, activity data or posture data; and records the secondary index in the HF monitoring log with the corresponding respiration COI. Optionally, the method may determine at least one of an activity index based on activity data or a posture index based on posture data. The method may record the at least one of activity index or posture index in the HF monitoring log with the corresponding respiration COI. The method may analyze the collection of respiration COI over the period of time with respect to baseline COI and may generate an indicator of potential heart failure based on a relation between the collection of respiration COI and baseline COI.

Optionally, the method may maintain a counter of a number of the multiple respiration cycles for which the respiration COI exceeds the corresponding baseline COI and may generate the indicator of potential heart failure when the counter exceeds a count threshold. The method may select between first and second baseline COI based on at least one of an activity index or a posture index. The filtering operation may apply a low pass filter to the CA data to obtain the respiration data.

In accordance with embodiments herein, a system is provided to monitor for potential heart failure (HF). The system comprises at least one processor and a memory coupled to the at least one processor. The memory stores program instructions. The program instructions are executable by the at least one processor to obtain cardiac activity data for multiple cardiac cycles, filter the cardiac activity data to obtain respiration data indicative of a respiration pattern, analyze the respiration data to determine one or more respiration characteristics of interest (COI), record the respiration COI along with collection time information concerning when the CA data was obtained and repeat the operations at a) to d) to form an HF monitoring log that includes a collection of respiration COI over a period of time.

Optionally, an implantable device may have a housing that encloses the memory and the at least one processor. The implantable device may include a transceiver to wirelessly transmit the HF monitoring log to an external device. The implantable device may comprise a sensor that may be configured to obtain at least one of activity data or posture data. The at least one processor may be configured to determine at least one of an activity index based on the activity data or a posture index based on the posture data.

The at least one processor may be configured to record the at least one of activity index or posture index in the HF monitoring log with the corresponding respiration COI.

Optionally, the at least one processor may be configured to analyze the collection of respiration COI over the period of time with respect to baseline COI. The processor may generate an indicator of potential heart failure based on a relation between the collection of respiration COI and baseline COI. An external device may have a transceiver that may be configured to receive the HF monitoring log and may have at least one processor configured to analyze the collection of respiration COI with respect to baseline COI to generate an indicator of potential heart failure based on a relation between the collection of respiration COI and baseline COI.

In accordance with embodiments herein a computer implemented method is provided for identifying respiration induced under sensing of cardiac events. The method is under control of one or more processors configured with specific executable instructions and obtains cardiac activity (CA) data for a cardiac cycle. The method detects whether an event of interest is present in the CA data, filters the cardiac activity data to obtain respiration data indicative of a respiration pattern, and analyzes the respiration data for respiration induced under detection of the event of interest from the CA data.

Optionally, the method may classify the cardiac cycle as abnormal cardiac activity when the event of interest was not detected as present in the CA data. The analyzing operation may include confirming or denying abnormal cardiac activity based on the respiration data. The filtering and analyzing operations may be performed when the detecting operation fails to detect the event of interest in the CA data. The method may obtain the respiration data from the CA data and may determine a respiration COI from the respiration data.

Optionally, the analyzing operation may further determine whether the respiration COI exceeds a threshold for a predetermined number of respiration cycles. The respiration COI may represent at least one of a peak to peak variation in the respiration data, a frequency of the respiration data, another indicators of tidal volume or morphology of the respiration data. The analyzing operation may compare the respiration data and the CA data for respiration induced filtering of the event of interest. Optionally the detecting operation detects whether the event of interest is present in the CA data based on a sensitivity threshold, the method further comprising adjusting the sensitivity threshold based on the respiration data.

In accordance with embodiments herein, an implantable cardiac monitor device is provided. The device comprises an electrode that is configured to obtain cardiac activity (CA) data for a cardiac cycle. A CA sensing circuit is configured to detect whether an event of interest is present in the CA data. A low pass filter (LPF) circuit is configured to filter the CA data to obtain respiration data indicative of a respiration pattern. The device further comprises at least one processor and a memory coupled to the at least one processor. The memory stores program instructions. The program instructions are executable by the at least one processor to analyze the respiration data for respiration induced under detection of the event of interest from the CA data.

Optionally, the at least one processor may be configured to adjust sensing parameters of the CA sensing circuit based on the respiration data. The at least one processor may be configured to adjust the sensing parameters by switching between first and second thresholds applied to the CA data. The device may further comprise a physiologic sensor circuit that may be configured to detect at least one of activity or posture data. The at least one processor may be configured to identify under detection of the event of interest based on the at least one of activity or posture data.

Optionally, the CA sensing circuit detects whether the event of interest is present in the CA data based on a sensitivity threshold, the at least one processor configured to identify under detection of the event of interest based on the respiration data, and in response thereto, adjust the sensitivity threshold.

DETAILED DESCRIPTION

The terms "abnormal cardiac activity" and "abnormal cardiac episodes" include, but are not limited to, bradycardia (slow heart rate), tachycardia (fast heart rate), asystole (no electrical heart activity), atrial or ventricular arrhythmias (problems with rate or rhythm of heart beat), and even atrial fibrillation (AF; very fast or irregular heart beat).

The terms "under sense", "under detect" and "under detection" refer to the condition in which the device fails to sense true cardiac activity. For example, cardiac data may be recorded that includes a QRS complex related to a normal/physiologic event, but the QRS complex may have a relatively small peak to peak amplitude. When the peak to peak amplitude falls below a predetermined threshold, the ICM may not recognize the QRS complex as a normal R-wave and will not count or label the R-wave as a normal event, thereby leaving an under-sensed gap in the cardiac activity.

The terms "false event detection" and "false detection" refer to incorrect identification and labeling (or lack of any detection or labeling) of an event. For example, an ICM may trigger a false bradycardia detection if one or more true QRS complex are under sensed.

In accordance with embodiments herein, ICM are provided to monitor patients for causes of abnormal heart activities such as potential episodes of bradycardia/asystole causing syncope, possible AF episodes causing cryptogenic stroke, potential episodes of atrial or ventricular arrhythmias causing intermittent chest palpitations and the like. Further, ICMs described herein monitor for heart failure (HF). The ICM detects electrical signal originated from the heart and attenuated by the lungs. The ICM is positioned within the body at a location above the heart such that, when the heart generates electrical signals, the signals pass through the lungs before reaching the ICM. In accordance with embodiments herein, the ICM collects cardiac activity (CA) data from ICM sensing electrodes. The detected CA data is low pass filtered to extract respiration data. The ICM analyzes the respiration data along with other data, such as activity and posture dada. For instance, respiration data may show increases directly or inversely proportional to increases in detected cardiac data amplitudes depending on vertical or horizontal patient position which is detected from a posture sensor. The changes in respiration data such as peak to peak values or other indicators of tidal volume can be used to monitor HF status.

Embodiments herein avoid high occurrences of false event detection that may otherwise occur due to factors, including respiration. Embodiments herein use low pass filtering to detect a size of respiration, which can be used to guide a search for the cause of false event detection along with other sensors such as activity and posture sensors. The respiration data can also be used to adjust sensing parameters.

Figure 1:
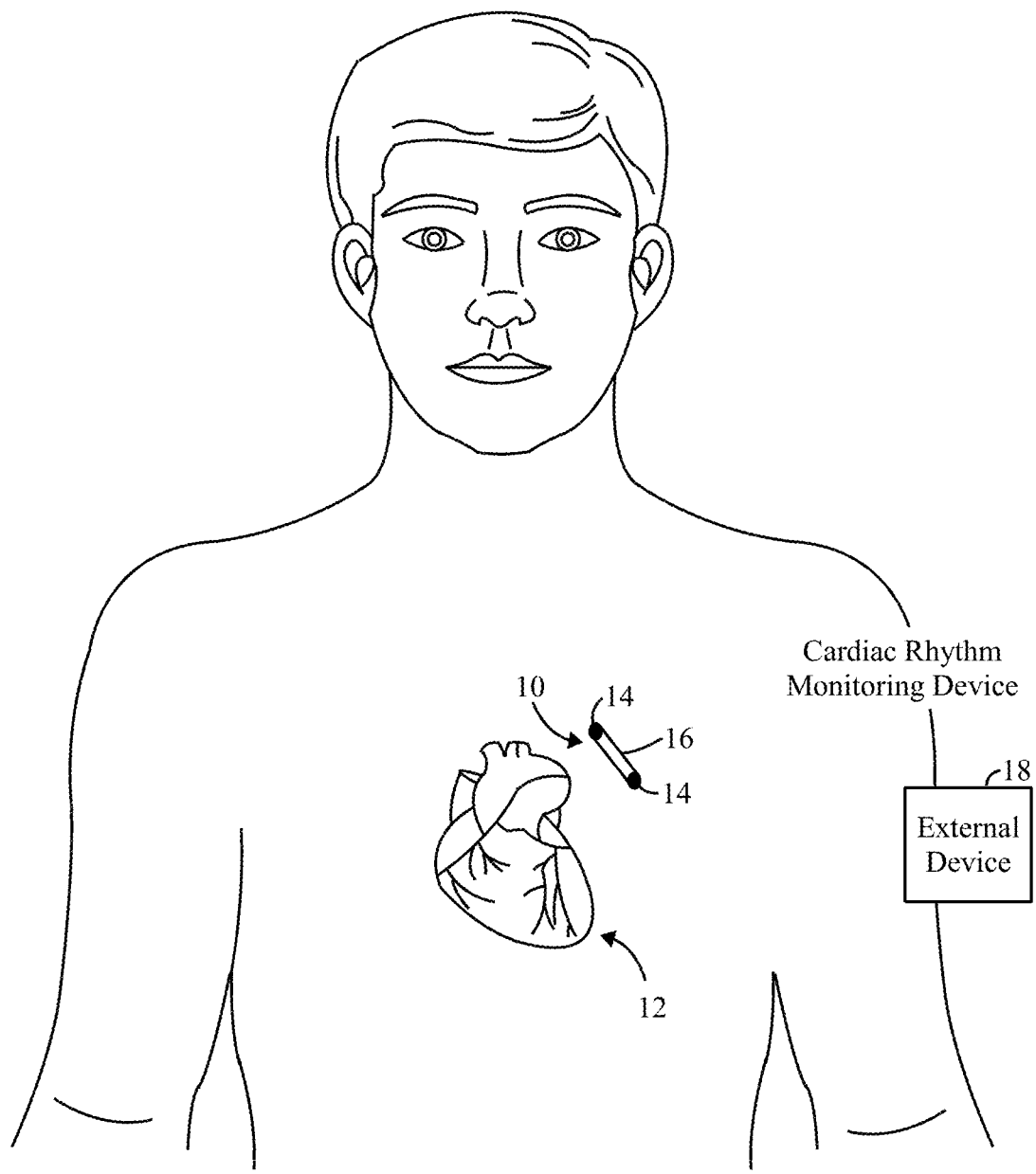
FIG. 1 illustrates an implantable cardiac rhythm monitoring (ICM) device intended for subcutaneous implantation at a site near the heart in accordance with embodiments herein.

FIG. 1 illustrates an implantable cardiac rhythm monitoring (ICM) device 10 intended for subcutaneous implantation at a site near the heart 12. The monitoring device includes a pair of spaced-apart sense electrodes 14 positioned with respect to a housing 16. The sense electrodes 14 provide for detection of far field electrogram signals. Numerous configurations of electrode arrangements are possible. For example, the electrodes 14 may be located on the same side of the housing 16. Alternatively, the electrodes 14 may be located on opposite sides of the housing 16. One of the electrodes 14 may be formed as part of the housing 16, for example, by coating all but a portion of the housing with a nonconductive material such that the uncoated portion forms the electrode. In this case, the other of the electrodes 14 may be electrically isolated from the housing electrode by placing it on a component separate from the housing, such as a header (not shown). In other configurations, the electrodes 14 may be located on short, stub leads extending away from the housing but coupled thereto through one or more headers so as to interface with internal components. The housing 16 includes various other components such as: sense electronics for receiving signals from the electrodes, a microprocessor for processing the signals in accordance with algorithms, such as the detection of abnormal cardiac activity, a loop memory for temporary storage of electrograms, a device memory for long-term storage of electrograms upon certain triggering events, sensors for detecting patient activity and a battery for powering components.

The monitoring device 10 senses far field, subcutaneous electrograms, processes the electrograms to detect arrhythmias and if an arrhythmia is detected, automatically records the electrograms in memory for subsequent transmission to an external device 18. Electrogram processing and arrhythmia detection is provided for, at least in part, by algorithms embodied in the microprocessor.

Figure 2A:
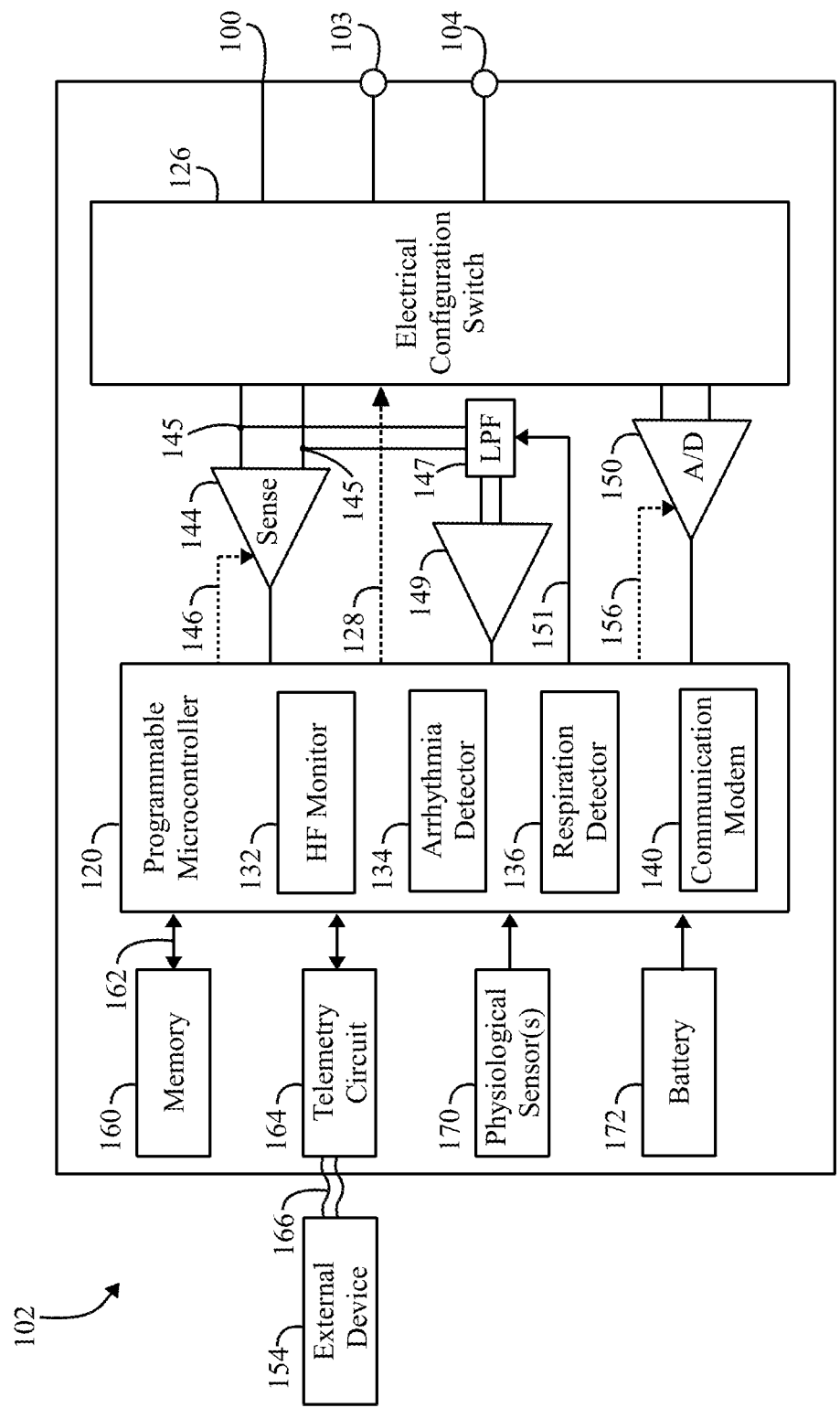
FIG. 2A illustrates a block diagram of an exemplary ICM that is configured to be implanted into the patient in accordance with embodiments herein.

FIG. 2A shows a block diagram of an exemplary ICM 102 (such as device 10) that is configured to be implanted into the patient. The ICM 102 is configured to monitor atrial activity, ventricular activity, or both ventricular and atrial activity through sensing circuitry. The ICM 102 has a housing 100 to hold the electronic/computing components. The housing 100 (which is often referred to as the "can", "case", "encasing", or "case electrode") may be programmably selected to act as an electrode for certain sensing modes. The housing 100 further includes a connector (not shown) with at least one terminal 103 and preferably a second terminal 104. The terminals 103, 104 may be coupled to sensing electrodes that are provided upon or immediately adjacent the housing 100. Optionally, more than two terminals 103, 104 may be provided in order to support more than two sensing electrodes to support a true bipolar sensing scheme using the housing as a reference electrode. Additionally or alternatively, the terminals 103, 104 may be connected to one or more leads having one or more electrodes provided thereon, where the electrodes are located in various locations about the heart. The type and location of each electrode may vary.

The ICM 102 is configured to be placed subcutaneously utilizing a minimally invasive approach. Subcutaneous electrodes are provided on the housing 100 to simplify the implant procedure and eliminate a need for a transvenous lead system. The sensing electrodes may be located on opposite sides of the device and designed to provide robust episode detection through consistent contact at a sensor-tissue interface. The ICM 102 may be configured to be activated by the patient or automatically activated, in connection with recording subcutaneous ECG signals. The ICM 102 includes a programmable microcontroller 120 that controls various operations of the ICM 102, including cardiac monitoring. Microcontroller 120 includes a microprocessor (or equivalent control circuitry), RAM and/or ROM memory, logic and timing circuitry, state machine circuitry, and I/O circuitry. The microcontroller 120 also performs the operations described herein in connection with collecting cardiac activity data and analyzing the cardiac activity data to identify respiration data and respiration COIs.

A switch 126 is optionally provided to allow selection of different electrode configurations under the control of the microcontroller 120. The electrode configuration switch 126 may include multiple switches for connecting the desired electrodes to the appropriate I/O circuits, thereby facilitating electrode programmability. The switch 126 is controlled by a control signal 128 from the microcontroller 120. Optionally, the switch 126 may be omitted and the I/O circuits directly connected to the housing 100 and a second electrode 103. Microcontroller 120 includes an HF monitor 132, an arrhythmia detector 134, and a respiration detector 136. The HF monitor 132 populates the HF monitor log and performs HF operations as described herein. The arrhythmia detector 134 is configured to analyze cardiac activity data and identify potential episodes, such as bradycardia or asystole causing syncope, possible AF episodes causing cryptogenic stroke (insufficient blood flow to the brain to meet metabolic demand), potential episodes of atrial or ventricular arrhythmias causing intermittent chest palpitations and the like. By way of example, the arrhythmia detector 134 may implement a detection algorithm as described in U.S. Pat. No. 8,135,456, the complete subject matter of which is incorporated herein by reference. The Respiration detector 136 is configured to analyze respiration activity data as explained herein. Although not shown, the microcontroller 120 may further include other dedicated circuitry and/or firmware/software components that assist in monitoring various conditions of the patient's heart and managing pacing therapies.

The ICM 102 is further equipped with a communication modem (modulator/demodulator) 140 to enable wireless communication. In one implementation, the communication modem 140 uses high frequency modulation, for example using RF or Blue Tooth telemetry protocols. The signals are transmitted in a high frequency range and will travel through the body tissue in fluids without stimulating the heart or being felt by the patient. The communication modem 140 may be implemented in hardware as part of the microcontroller 120, or as software/firmware instructions programmed into and executed by the microcontroller 120. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 102 includes sensing circuitry 144 selectively coupled to one or more electrodes that perform sensing operations, through the switch 126 to detect cardiac activity data indicative of cardiac activity. The sensing circuitry 144 detects events of interest from the cardiac activity data utilizing, among other things, a sensitivity threshold. As explained herein, the sensitivity threshold may be adjusted when the ICM 102 determines that the sensing circuitry 144 is under sensing events of interest. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. In one embodiment, switch 126 may be used to determine the sensing polarity of the cardiac signal by selectively closing the appropriate switches.

The output of the sensing circuitry 144 is connected to the microcontroller 120 which, in turn, determines when to store the cardiac activity data (digitized by the A/D data acquisition system 150) in the memory 160. For example, the microcontroller 120 may only store the cardiac activity data (from the A/D data acquisition system 150) in the memory 160 when a potential arrhythmia episode is detected. The sensing circuitry 144 receives a control signal 146 from the microcontroller 120 for purposes of controlling the gain, threshold, polarization charge removal circuitry (not shown), and the timing of any blocking circuitry (not shown) coupled to the inputs of the sensing circuitry. In the example of FIG. 2A, a single sensing circuit 144 is illustrated. Optionally, the ICM 102 may include multiple sensing circuits, similar to sensing circuit 144, where each sensing circuit is coupled to two or more electrodes and controlled by the microcontroller 120 to sense electrical activity detected at the corresponding two or more electrodes. The sensing circuit 144 may operate in a unipolar sensing configuration (e.g., housing 100 to electrode 103) or in a bipolar sensing configuration (e.g., between electrodes 103 and 104 referenced to the housing electrode 100). Optionally, the sensing circuit 144 may be removed entirely and the microcontroller 120 perform the operations described herein based upon the EGM signals from the A/D data acquisition system 150 directly coupled to the electrodes 100, 103, and/or 104.

The sensing circuit 144 includes input lines that carry the cardiac activity data sensed by the electrodes. The input lines of the sensing circuit 144 are joined at nodes 145 to inputs of a low pass filter (LPF) circuit 147. The LPF circuit 147 processes the cardiac activity data as described herein to form respiration data. The output of the LPF circuit is coupled to an A/D converter 149 and outputs the respiration data to the A/D converter 149. The A/D converter 149 converts analog respiration data into a digital form that is provided to the microcontroller 120 for analysis and storage in memory 160. The embodiment of FIG. 2A illustrates the input lines to the sensing circuit 144 and LPF circuit 147 to carry analog signals. Optionally, the input lines of the sensing circuit 144 and LPF circuit 147 may carry digital signals, in which case the sensing circuit 144 and LPF circuit 147 are configured to process digital CA data. When the LPF circuit 147 receives digital CA data as an input, the LPF circuit 147 outputs the respiration data in digital form and, the A/D convert 149 may be omitted.

By way of example, the LPF circuit 147 may be defined to pass a low frequency envelope of the CA data. For example, the LPF circuit 147 may be a Butterworth Low Pass Filter having the following filter parameters: Astop=30 dB, Apass=1 dB, Fpass=0.3 Hz, and Fstop=1 Hz. Optionally, alternative types of filters and filter parameters may be utilized. Further, the microcontroller 120 is coupled to the LPF circuit 147 through a feedback line 151 to allow the microcontroller 120 to modify the filter parameters of the LPF circuit 147 automatically and iteratively during operation (e.g., see FIG. 7).

Figure 2B:
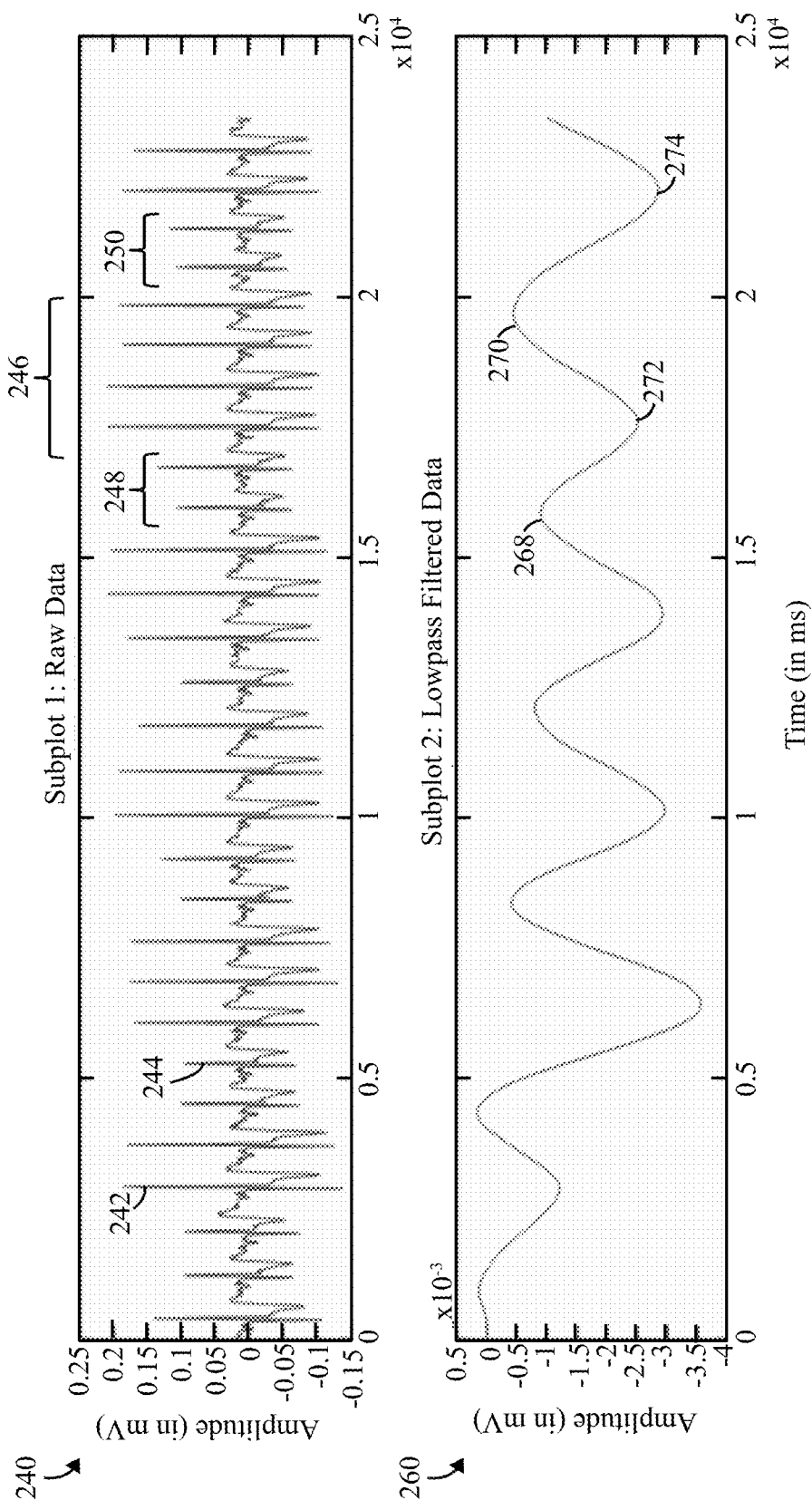
FIG. 2B illustrates examples of cardiac activity data and respiratory data, respectively that may be obtained in accordance with embodiments herein.

FIG. 2B illustrates examples of cardiac activity data and respiratory data, respectively, that may be obtained in accordance with embodiments herein. The cardiac activity data is illustrated as signal 240 where the amplitude of the CA data varies between −0.14 mV and 0.22 mV. The signal 240 extends over a period of time (e.g., several seconds) during which multiple cardiac cycles/episodes occur, with each cardiac cycle having at least one cardiac event of interest. In the example of FIG. 2B, the cardiac events of interest represent intrinsic R waves that are detected with different amplitude or peak to peak variations. For example, the R-wave 242 has a peak to peak variation between approximately −0.14 mV and 0.18 mV, while R-wave 244 has a peak to peak variation extending between −0.08 mV and 0.08 mV. The amplitudes of the R-wave within the CA data vary in a somewhat repeating manner between larger amplitudes, such as in the region 246, and smaller amplitudes, such as in regions 248, 250. One or more of the cardiac events 244 having low peak to peak variation may not be accurately declared to represent an intrinsic cardiac event. Instead, cardiac events 244 with low peak to peak variation (e.g., in regions 248, 250) may be "under sensed" and classified as non-events or abnormal cardiac events, thereby appearing as a non-event gap between normal cardiac events.

As described herein, the CA data is filtered by the LPF circuit 147 to form respiratory data. FIG. 2B illustrates respiratory data as signal 260 that follows a generally sinusoidal pattern between a series of local peaks (e.g., 268, 270) and local valleys (e.g., 272, 274) that vary between approximately 0.0 mV and −3.5 mV. It is recognized that the voltage ranges, negative versus positive voltages and the like may vary. The local peaks for the respiratory data generally correspond to the segments of the CA data that exhibit low peak to peak variation in connection with events of interest. For example, the local peaks 268, 270 in the respiratory data generally correspond in time to the regions 248, 250 in the CA data where relatively small peak to peak variation is exhibited in connection with each R-wave.

In connection with the patient's breathing behavior, the local peaks in the respiratory data correspond to maximum points in inspiration phases of breathing cycles (e.g., a transition point between the end of inhalation and the beginning of exhalation). The local valleys in the respiratory data correspond to minimum points of expiration phases of breathing cycles (e.g., a transition point between the end of exhalation and the beginning of inhalation). As explained herein, respiration characteristics of interest (COI) are derived from the respiration data (e.g., peak to peak variation, respiration frequency). The respiration characteristics of interest are used to determine whether activity within the CA data at 240 should be treated as intrinsic cardiac events or or abnormal cardiac events.

Figure 2C:
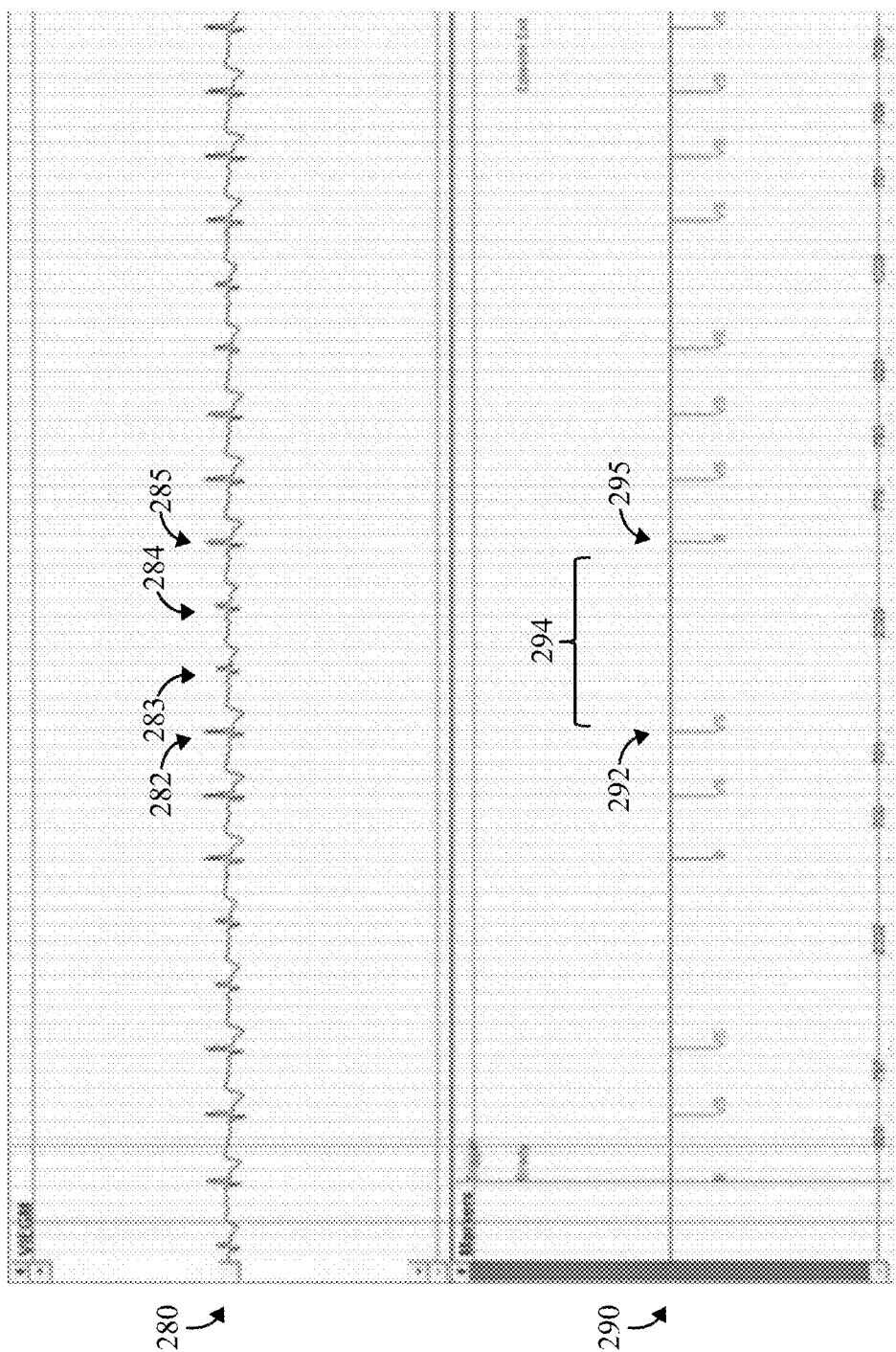
FIG. 2C illustrates an example of cardiac activity data and potential related event markers that may be labeled and mis-labeled without the respiration induced under sending processes described herein.

FIG. 2C illustrates an example of cardiac activity data and potential related event markers that may be labeled and mis-labeled without the respiration induced under sending processes described herein. The cardiac activity data 280 may be sensed over a select time period. The event markers 290 are assigned to each corresponding event of interest (and non-event) from the cardiac activity data 280. The cardiac activity data 280 includes events of interest, such as events 282-285. As illustrated in FIG. 2C, events 282-285 exhibit different peak to peak amplitudes, due in part to the influence of patient respiration upon the physical surroundings of the ICM. The respiration signal modulates R-wave amplitudes. A breath occurs over a respiratory cycle that includes one inspiration phase (inhalation) and one expiration phase (exhalation). As a patient breathes, the chest expands and contracts, which causes the ICM to move relative to the heart. The lungs inflate and deflate, resulting in alternating increases and decreases in an amplitude of an ECG signal detected by the ICM.

Absent implementation of the processes described herein, the ICM may disregard or under sense the events 283-285. The ICM detects and correctly classifies the event 282 as an intrinsic ventricular sensed event, as denoted by a ventricular sense event 292. However, the amplitudes of the events 283-284 may be too small to be detected (e.g., do not satisfy a threshold) and labeled as intrinsic ventricular events by an ICM, but does not implement the respiration correction processes described herein. When the events 283-284 fall below that detection threshold, the events 283-284 are not labeled within the event markers series 290 (as denoted by the gap 294). Event 285 is detected with sufficient amplitude to be labeled as an intrinsic event by the ICM. However, the gap 294 extends for a period of time, during which the ICM does not detect a intrinsic ventricular event. The gap 294 exceeds a R-R interval and thus the ICM includes a bradycardia marker 295 within the event markers 290. It is recognized that alternative marking rules and processes may be utilized. The example of FIG. 2C is merely intended to exhibit one example of how an ICM may miss-label events in connection with under sensing. As explained herein, at least in accordance with the processes of FIGS. 6 and 7, potential under sensing may be identified and the events 283-285 may be correctly classified as normal intrinsic ventricular sensed events.

Figure 2D:
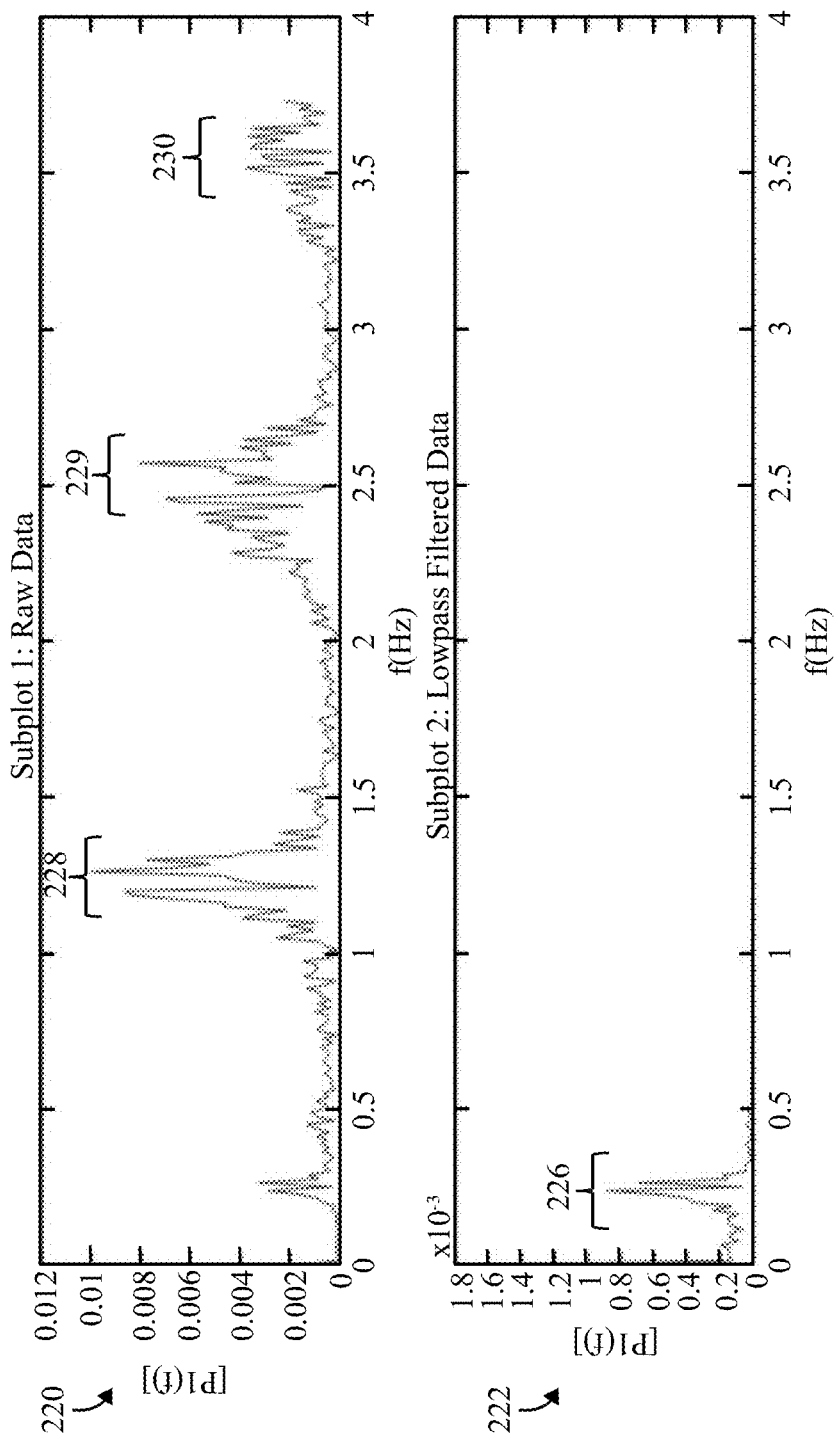
FIG. 2D illustrates example frequency spectrums that may be present in connection with CA data and respiration data in accordance with embodiments herein.

FIG. 2D illustrates example frequency spectrums that may be present in connection with CA data and respiration data. A Fast Fourier Transform 220 illustrates the frequency content of CA data, where the frequency content extends over a substantial frequency range. A Fast Fourier Transform 222 illustrates the frequency content of respiration data that may be collected by low-pass filtering the CA data. The frequency content of the respiration data appears in a relatively short frequency band 226, while the frequency content of the CA data includes multiple spikes (e.g., in frequency bands 228-230). The FFT amplitude spectrum clearly shows that the respiration signal frequencies are the lowest frequencies with significant amplitudes before the highest amplitudes.

Returning to FIG. 2A, the ICM 102 further includes an analog-to-digital A/D data acquisition system (DAS) 150 coupled to one or more electrodes via the switch 126 to sample cardiac signals across any pair of desired electrodes. The data acquisition system 150 is configured to acquire cardiac electrogram (EGM) signals, convert the raw analog data into digital data, and store the digital data for later processing and/or telemetric transmission to an external device 154 (e.g., a programmer, local transceiver, or a diagnostic system analyzer). The data acquisition system 150 is controlled by a control signal 156 from the microcontroller 120.

The microcontroller 120 is coupled to a memory 160 by a suitable data/address bus 162. The programmable operating parameters used by the microcontroller 120 are stored in memory 160 and used to customize the operation of the ICM 102 to suit the needs of a particular patient. Such operating parameters define, for example, detection rate thresholds, sensitivity, automatic features, arrhythmia detection criteria, activity sensing or other physiological sensors, and electrode polarity, etc.

In addition, the memory 160 stores the cardiac activity data, as well as the markers and other data content associated with detection of episodes. The operating parameters of the ICM 102 may be non-invasively programmed into the memory 160 through a telemetry circuit 164 in telemetric communication via communication link 166 with the external device 154. The telemetry circuit 164 allows intracardiac electrograms and status information relating to the operation of the ICM 102 (as contained in the microcontroller 120 or memory 160) to be sent to the external device 154 through the established communication link 166. In accordance with embodiments herein, the telemetry circuit 164 conveys the cardiac activity data, markers and other information related to episodes. By way of example, the external device 154 may represent a bedside monitor installed in a patient's home and utilized to communicate with the ICM 102 while the patient is at home, in bed or asleep. The external device 154 may be a programmer used in the clinic to interrogate the device, retrieve data and program detection criteria and other features. The external device 154 may be a device that can be coupled over a network (e.g., the Internet) to a remote monitoring service, medical network and the like. The external device 154 facilitates access by physicians to patient data as well as permitting the physician to review real-time ECG signals while being collected by the ICM 102.

The ICM 102 may further include magnet detection circuitry (not shown), coupled to the microcontroller 120, to detect when a magnet is placed over the unit. A magnet may be used by a clinician to perform various test functions of the ICM 102 and/or to signal the microcontroller 120 that the external device 154 is in place to receive or transmit data to the microcontroller 120 through the telemetry circuits 164.

The ICM 102 can further include one or more physiologic sensor 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). The physiologic sensor 170 is configured to generate activity data and/or posture data that are passed to the microcontroller 120 for analysis and optional storage in the memory 160 in connection with the cardiac activity data, markers, episode information and the like. The physiologic sensor 170 is also configured to sense heart sounds that are used as described herein. While shown as being included within the ICM 102, the physiologic sensor(s) 170 may be external to the ICM 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 102. The battery 172 is capable of operating at low current drains for long periods of time. The battery 172 also desirably has a predictable discharge characteristic so that elective replacement time can be detected. As one example, the ICM 102 employs lithium/silver vanadium oxide batteries. The battery 172 may afford various periods of longevity (e.g., three years or more of device monitoring). In alternate embodiments, the batter 172 could be rechargeable. See for example, U.S. Pat. No. 7,294,108, Cardiac event microrecorder and method for implanting same, which is hereby incorporated by reference.

The ICM 102 provides a simple to configure data storage option to enable physicians to prioritize data based on individual patient conditions, to capture significant events and reduce risk that unexpected events are missed. The ICM 102 may be programmable pre- and post-trigger event storage. For example, the ICM 102 may be automatically activated to store 9-60 seconds of activity data prior to an event of interest and/or to store 9-60 seconds of post event activity. Optionally, the ICM 102 may afford patient triggered activation in which pre-event activity data is stored, as well as post event activity data (e.g., pre-event storage of 1-15 minutes and post-event storage of 30-60 seconds). Optionally, the ICM 102 may afford manual (patient triggered) or automatic activation for EGM storage. Optionally, the ICM 102 may afford additional programming options (e.g., asystole duration, bradycardia rate, tachycardia rate, tachycardia cycle count). The amount of EGM storage may vary based upon the size of the memory 160.

The ICM 102 may provide comprehensive safe diagnostic data reports including a summary of heart rate, in order to assist physicians in diagnosis and treatment of patient conditions. By way of example, reports may include episode-related diagnostics for auto trigger events, episode duration, episode count, episode date/time stamp and heart rate histograms. The ICM 102 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 3A:
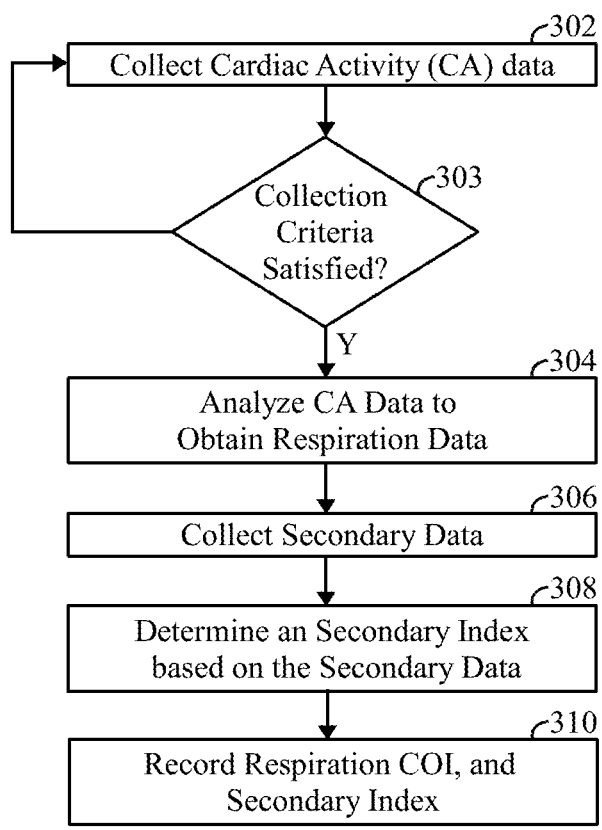
FIG. 3A illustrates a computer implemented process monitoring for indications of heart failure in accordance with embodiments herein.

Next, various processes are described in connection with embodiments herein that are performed by one or more of the circuits, processors and other structures illustrated in the figures and described in the specification. The operations of the processes described herein may be implemented wholly or in part by one or more circuits and/or processors within an ICM, a local external device (e.g., bedside monitor, smart phone, tablet device, clinician programmer, etc.), a remote server (as part of a hospital network), and the like. FIG. 3A illustrates a computer implemented process monitoring for indications of heart failure in accordance with embodiments herein. The operations of FIG. 3A may be implemented at different times and based on various criteria, such as when cardiac activity data has been analyzed by a detection module (e.g., arrhythmia detector 134 in FIG. 2) and a potential episode has been identified. Optionally, the operations of FIG. 3A may be implemented independent of detection of potential episodes in a current set of cardiac activity data. For example, the operations may be implemented at predetermined times based on a programmed schedule, on a periodic basis, based on patient activity, patient posture and the like.

At 302, one or more processors collect cardiac activity data. For example, the CA data may be derived from sensor signals sensed at the electrodes on the ICM. At 302, the processors may analyze the CA data for one or more criteria of interest and/or store the CA data (e.g., in a first-in first-out buffer). The processors may be within the ICM, an external device or located at a remote server. When the processors are at an external device or remote server, the CA data is transmitted from the ICM to the external device and/or remote server.

At 303, the one or more processors determine whether one or more respiration data collection criteria are satisfied. For example, it may not be desirable or necessary to collect respiration data at the same time, or every time, that the processes collect CA data. Instead, one or more collection criteria may be defined (e.g., preprogrammed or automatically updated). By way of example, the decision at 303 may determine to collect respiration data periodically, along with activity and posture data. For example, the collection criteria may define respiration data to be collected during scheduled time windows (e.g., at select times each day or each week, at the top of each hour, when the patient wakes up, has meals, goes to bed, and the like). Additionally or alternatively, other collection criteria may be defined such as one or more particular postures and/or activity states. For example, at specific times of day, the processors may open the scheduled time window and determine whether the patient is at rest and in a sitting posture.

Additionally or alternatively, the collection criteria may be in response to detection of particular types of cardiac activity, postures and/or physiologic activity. For example, the collection criteria may be satisfied when a patient lays down for a predetermined minimum period of time, remains standing for a predetermined period of time, undergoes moderate or high activity for a predetermined period of time, and the like. Additionally or alternatively, the collection criteria may be satisfied when the ICM detects certain characteristics in the cardiac activity, such as particular types of episodes, a predetermined number of cardiac cycles in which a P-wave, R-wave, or QRS complex are not detected, and the like. Optionally, the decision at 303 may be omitted entirely At 303, when the collection criteria are not satisfied, flow returns to 302 and the IMD continues to collect cardiac activity data. Alternatively, when the collection criteria are satisfied, flow advances to 304. At 304, the CA data is analyzed to obtain respiration data indicative of respiration activity of the patient. For example, the CA data may be passed through a low-pass filter circuit to form a respiration signal of respiration data. The respiration data may be generated by a hardware low-pass filter circuit that receives analog or digitized CA signals from the electrodes on the ICM. Optionally, the low-pass filter circuit may be implemented as a software module within the one or more processors of the ICM. For example, the CA data may be digitized and stored in memory. The processors may apply a low-pass filter circuit to the stored CA data to output respiration data that is also stored in the memory.

Also, at 304, the respiration data is analyzed for one or more respiration characteristics of interest. For example, the one or more processors may analyze the respiration data to identify positive and negative peak values therein and based thereon, calculate one or more peak to peak respiration values or other indicators of tidal volume. The peak to peak respiration values, alone or in combination with the complete stream of respiration data, may represent the respiration characteristic of interest. Additionally or alternatively, the processors may analyze the respiration data for other respiration characteristics of interest, such as frequency, morphology and the like.

At 306, the one or more processors collect secondary data, such as heart sound data, activity data and/or posture data. For example, a signal output by the physiologic sensors 170 may be analyzed to determine a level of activity that the patient is undergoing and/or to determine a posture of the patient. As a further example, the output of the physiologic sensor 170 may be used to collect the heart sound signals from electrical signals that contain acceleration of myocardium mass and blood flow.

At 308, the one or more processors analyze the secondary (e.g., heart sound, activity and/or posture) data to determine one or more corresponding index (e.g., a heart sound index, an activity index and/or a posture index, respectively). For example, the activity data may be compared to one or more thresholds, with each threshold having an associated activity index value. Based upon the relation between the activity data and the thresholds, an activity index may be assigned thereto (e.g., no activity, low activity, medium activity, high activity). Similarly, the posture data may be compared to one or more thresholds, with each threshold having an associated posture index value. Based on the relation between the posture data and the thresholds, a posture index may be assigned thereto (e.g., standing, sitting, reclining, horizontal).

Figure 3B:
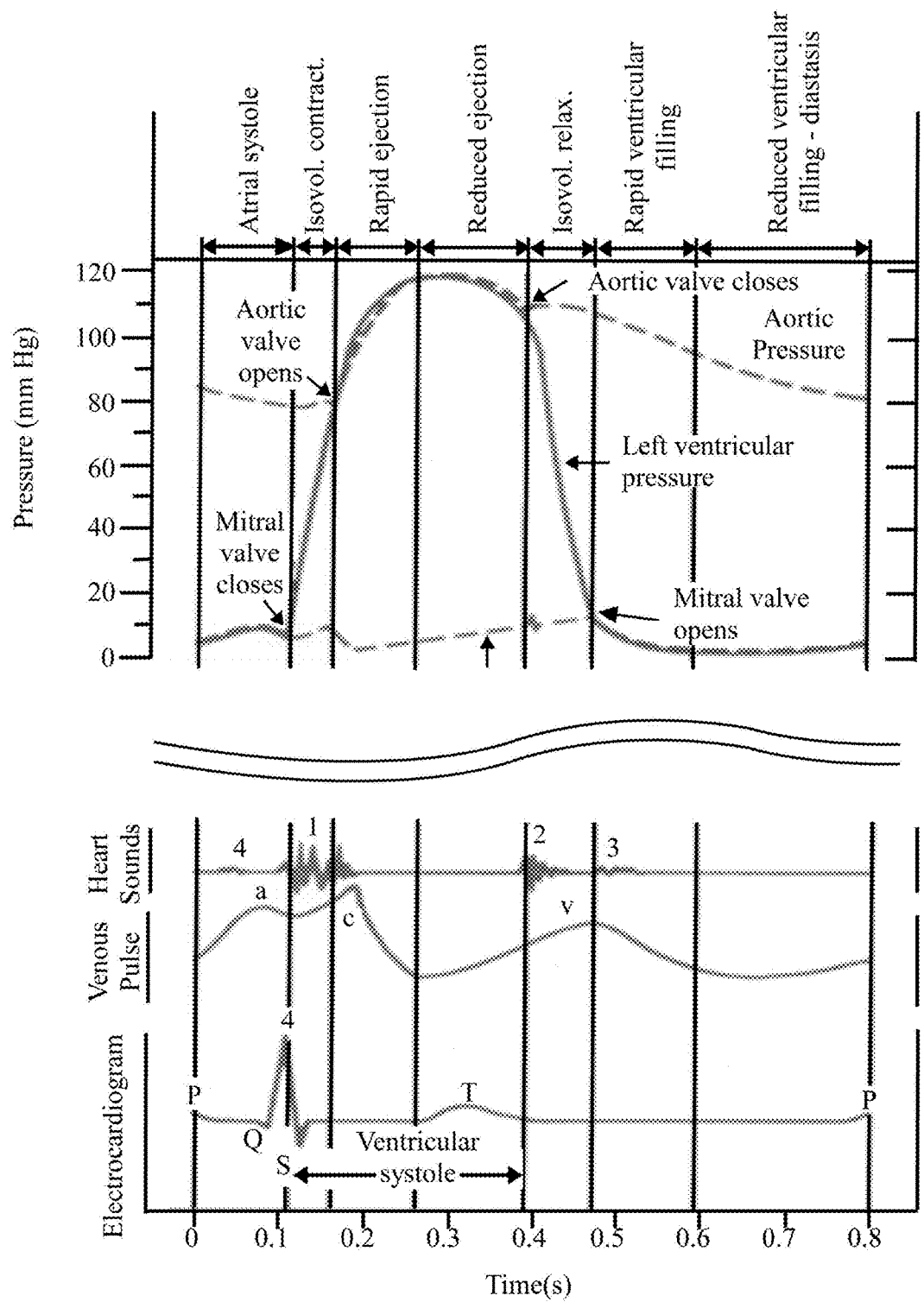
FIG. 3B illustrates graphs showing a relation between various characteristics of heart activity.

Optionally, the respiration signals can be combined with heart sounds for monitoring HF progression. FIG. 3B illustrates graphs showing a relation between various characteristics of heart activity. Among other things, FIG. 3B illustrates left ventricular pressure, heart sounds, venous pulse and an electrocardiogram over the phases of the cardiac cycle, The heart sound S1 refers to the first heart sound that mainly results from the closing of mitral valves at the beginning of ventricular systole. During start of systole, papillary muscles attached to the mitral valve leaflets contract via chordae tendineae. In turn, the chordae tendineae abruptly tenses and prevents the backflow of blood into lower pressure atrial area. The sudden chordae tendineae tensing and the ventricular squeezing against closed semilunar valve (e.g., aortic valve) sends blood back toward the left atrium and the mitral valve closes shut by catching the rushing blood with the leaflets. In summary, the S1 sound is mainly caused by the prolongation of sound within the blood associated with this sudden block of flow reversal. It is a function of the force of ventricular contraction and the distance between the valve leaflets. The vibration and acceleration from the flow through the gaps of leaflets may contain different frequency components from the wall motion which may be filtered out through a filter design. The IMD filters the output of the physiologic sensor 170 to obtain the frequency component of interest. Additionally or alternatively, the IMD may process the raw S1 sound, where a peak amplitude of the S1 sound is related to sudden rise in pressure from the baseline or the contractility of ventricles.

The S3 heart sound represents the third heart sound, also known as the "ventricular gallop," occurs at the beginning of diastole just after the S2 sound when the mitral valve opens, allowing passive filling of the left ventricle. The S3 sound is produced by the large amount of blood striking a very compliant left ventricle and the S3 sound indicates increased volume of blood within the ventricle. The presence of an S3 sound is often a sign of systolic heart failure, but it may sometimes be a normal finding. An existence of S3 sound can be an important sign of systolic heart failure because, in the present setting, the myocardium is usually overly compliant, resulting in a dilated LV.

In accordance with embodiments herein, the processor of the IMD may analyze heart sounds to identify characteristics of interest such as a change in a maximum/peak in the S1 heart sound and/or existence of a S3 heart sound. When a heart sound characteristic of interest is identified, the corresponding secondary index is determined. For example, the secondary index may indicate a peak level for S1, a presence of S3, a duration of S3 and the like. Due to the close relationship between heart sound and hemodynamics of the heart and electrocardiogram (FIG. 1), heart sound can be used to access hemodynamics potentially.

At 310, the one or more processors record in memory (e.g., an HF monitoring log), collection time information (e.g., a time and date at which the CA data and respiration data were collected). The HF monitoring log also records the respiration COI and secondary index (e.g., heart sound index, activity index and posture index). Optionally, the HF monitoring log may also include the CA data, the heart sound data and/or respiration data.

Figure 4:
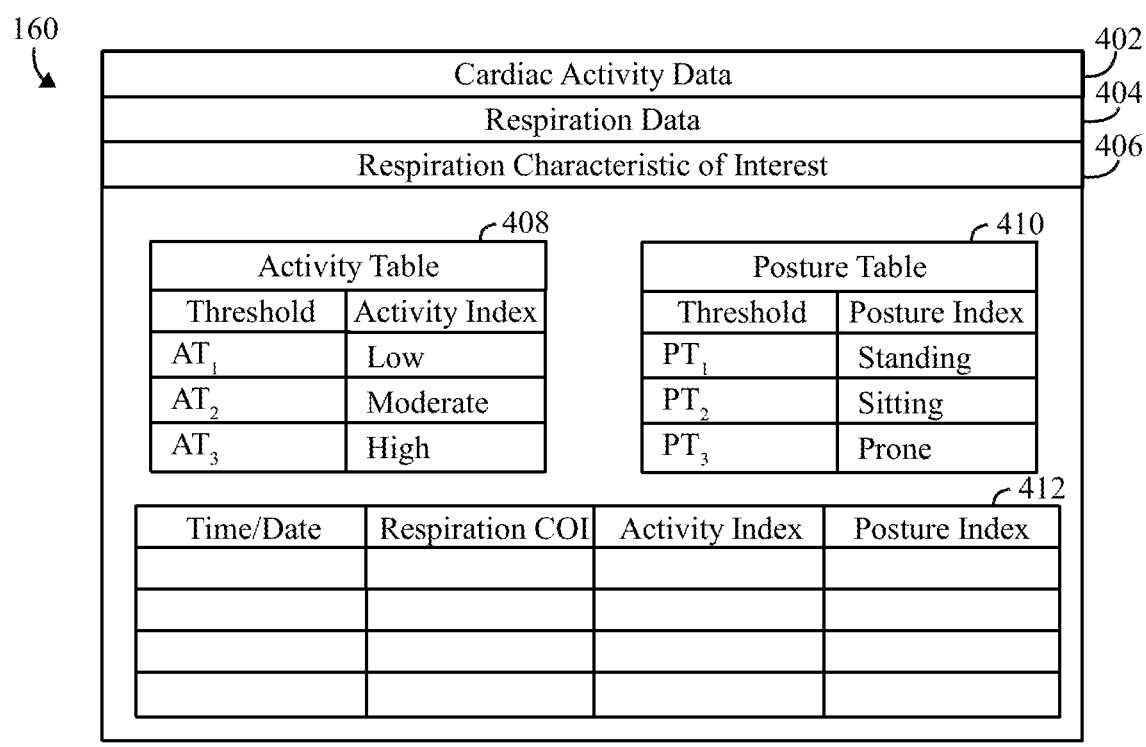
FIG. 4 illustrates a section of memory that stores information in connection with the operations of FIG. 3A in accordance with embodiments herein.

FIG. 4 illustrates a section of memory (e.g., memory 160 in FIG. 2A) that stores information in connection with the operations of FIG. 3A. The memory 160 may be configured to store cardiac activity data 402 for a predetermined period of time, such as a select number of cardiac cycles. For example, the cardiac activity data 402 may be stored in a first-in first-out buffer having a length sufficient to record the cardiac activity data for one minute, five minutes, 30 seconds, 50 heartbeats, 25 heartbeats, etc. The memory 160 also stores the respiration data 404 that is generated based upon the analysis of the cardiac activity data. The memory 160 also stores the respiration characteristics of interest 406 that are determined from the respiration data 404. For example, the respiration COI 406 may represent a series of peak to peak variations measured between successive peaks in the respiration data 404. When multiple peak to peak values are measured, a maximum peak to peak value may be selected. Additionally or alternatively, an average or another mathematical combination of the peak to peak values may be determined. Optionally, the respiration COI 406 may represent a single peak to peak value.

The memory 160 further stores an activity table 408 that may be preprogrammed to contain thresholds to designate transitions between different levels of activity. For example, thresholds AT1-AT3 may be used to distinguish between low, moderate and high activity indexes, respectively. The memory 160 further stores a posture table 410 that may be preprogrammed to contain thresholds to designate transitions between different postures. For example, thresholds PT1-PT3 may be used to distinguish between a standing posture, sitting posture and prone posture, respectively. The activity and posture tables 408, 410 are referenced in connection with the operations of FIG. 3A to determine an activity and posture index associated with the present cardiac activity data 402, respiration data 404 and respiration COI 406. In accordance with the operations of FIG. 3A, at 310, the current respiration COI, activity index and posture index are recorded in a HF monitoring log 412, along with a time/date stamp. Additionally or alternatively, the memory 160 and/or HF monitoring log 412 may store heart sound data, heart sound indexes and the like. The HF monitoring log 412 maintains a record of changes in the respiration data over time.

Over time, the HF monitoring log 412 is populated with multiple data sets. The data from the HF monitoring log 412 may be transmitted wirelessly from the ICM at select times, such as on a day-to-day basis, weekly, monthly and the like. Optionally, the HF monitoring log 412 may be wirelessly conveyed to an external device on a demand basis (e.g., in response to a patient instruction to the ICM, an instruction from a bedside external device, patient controlled external device, clinician external device and the like). The ICM may transmit the data from the HF monitoring log 412 to a bedside monitoring external device, a smart phone, or other external device that is configured to wirelessly communicate with the ICM. The external device may analyze the HF monitoring log for certain criteria. For example, when pulmonary edema is developed, a size of the respiration signals will decrease due to fluid buildup and overload within the lungs. As the fluid builds up in the lungs, the two peak values within the respiration data will decrease over time. Accordingly, a series of successive entries in the HF monitoring log 412 may exhibit a common type of activity or posture, but with progressively decreasing peak to peak variations in the respiration data. When the foregoing pattern is exhibited, methods and systems herein may designate a potential development of pulmonary edema, and in response thereto, direct the patient to take appropriate corrective actions (e.g., consult a physician, change medications, etc.).

Different patients may exhibit differences in the values and relations of respiration characteristics of interest in connection with cardiac activity data. For example, patients with different physical characteristics (weight, height, age, gender) will experience differences in the values and relations of respiration characteristics of interest with respect to cardiac activity data. In accordance with embodiments herein, baseline respiration information may be collected from individual patients. For example, the operations of FIG. 3A may be performed once or periodically to collect baseline respiration data for a patient in which a particular ICM is implanted. The baseline respiration data is used to derive baseline respiration characteristics of interest (e.g., baseline peak to peak values and the like), relative to particular postures and/or activity levels. Additionally or alternatively, the baseline information may be collected when a patient undergoes particular postures for a predetermined period of time, changes in posture, activity states and the like. For example, during a baseline establishment phase, each time a patient lays down, the ICM may collect respiration data and respiration COI. During the baseline establishment phase, the ICM may collect the respiration data and COI when certain activity levels are detected and/or other posture states are detected. The baseline information may be then combined to form baselines for each potential posture state (e.g., when standing, sitting, prone, supine, etc.) and/or various potential activity states (e.g., low, moderate, high). The baseline information may be then used later, in connection with analyzing data in the HF monitoring log to determine relative changes of an individual patient over time.

Figure 5:
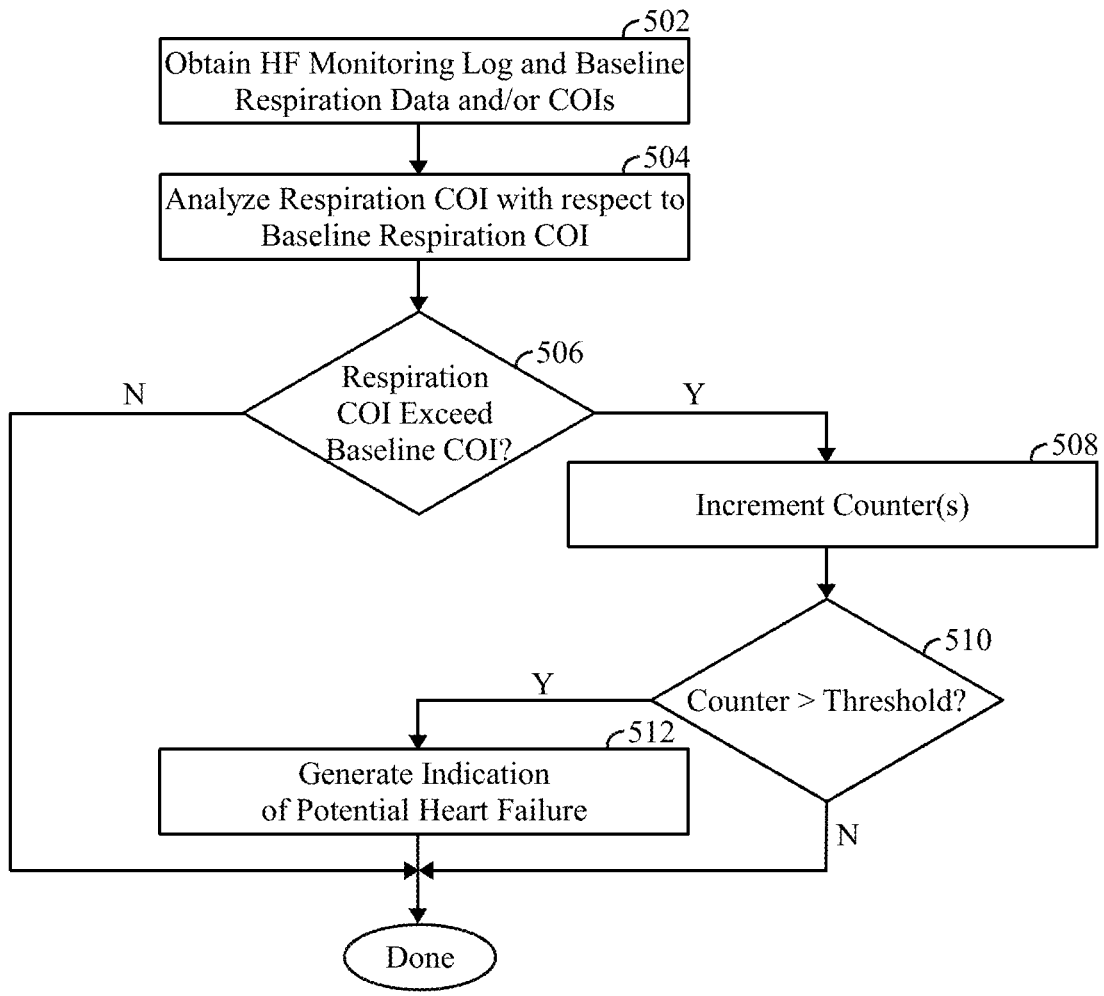
FIG. 5 illustrates a process for detecting potential heart failure based on respiration data collected over time in accordance with embodiments herein.

FIG. 5 illustrates a process for detecting potential heart failure based on respiration data collected over time. The operations of FIG. 5 may be implemented wholly or in part by one or more circuits and/or processors within an ICM, a local external device (e.g., bedside monitor, smart phone, tablet device, clinician programmer, etc.), a remote server (as part of a hospital network), and the like. The operations of FIG. 5 may be implemented based on various criteria, such as when cardiac activity data has been analyzed by a detection module (e.g., arrhythmia detector 134 in FIG. 2) and a potential episode has been identified. Optionally, the operations of FIG. 5 may be implemented independent of detection of potential episodes in a current set of cardiac activity data. For example, the operations may be implemented at predetermined times based on a programmed schedule, on a periodic basis, based on patient activity, patient posture and the like.

At 502, the one or more processors obtain an HF monitoring log and optionally obtain baseline respiration data and/or COI for a particular patient. The baseline information may be specific to the patient, as captured by an ICM within the patient. Alternatively, the baseline information may be generally defined for a patient population (e.g., a patient population having similar gender, height, weight, age characteristics). Optionally, the baseline information may be specified in other manners (e.g., program by a clinician).

At 504, the one or more processors analyze the respiration COI with respect to baseline respiration COI. For example, the baseline respiration COI may represent preprogrammed thresholds for the peak to peak interval, respiration frequency and the like. When the peak to peak interval and/or respiration frequency/rate cross a corresponding threshold, this may represent an indication of potential congestive heart failure. Additionally or alternatively, the baseline respiration COI may be patient specific, and collected by the ICM as explained herein. Additionally or alternatively, the baseline respiration COI may represent an acceptable range at which a corresponding characteristic may vary over time. For example, it may be determined that a baseline peak to peak interval should only vary within a desired range for any given posture, heart sound and activity level. As another example, the baseline respiration COI may represent an acceptable range for breathing rate/frequency for a given posture and activity state. The analysis at 504 may compare the information from the log with the baseline COI and, when a difference there between exceeds acceptable limits/thresholds, the processors may determine that potential congestive heart failure is occurring.

At 506, the one or more processors determine whether the respiration COI exceeds the corresponding baseline COI. The baseline COI may be selected in part based on the posture index and/or activity index. For example, a first baseline COI may be utilized when the activity index indicates low activity and/or the posture index indicates a prone position, while a second baseline COI may be utilized when the activity index indicates high activity and/or and the standing position index indicated a standing position. As another example, the baseline COI may utilize a peak threshold for S1 and/or a threshold for S3. When the respiration COI exceeds the baseline COI, flow moves to 508. Otherwise, the process of FIG. 5 ends. At 508, the one or more processors increment one or more counters. The counter(s) track the number of times that the respiration data exceeds a corresponding baseline or threshold. For example, the count at 508 may count the number of episodes in which the peak to peak interval in the respiratory data falls below a minimum threshold. Additionally or alternatively, the counter may track the number of episodes in which the breathing rate exceeds a minimum threshold that would otherwise be expected when the patient is experiencing a particular level of activity and in a particular posture. At 510, the one or more processors determine whether the counter has exceeded a threshold. When the counter or counters exceed the corresponding thresholds, flow moves to 512. Otherwise, the process of FIG. 5 ends.

At 512, the one or more processors generate an indicator of potential heart failure. For example, when the peak to peak intervals from the respiration data from the HF monitoring log exhibit more variation than the desired range, the one or more processors generate an indication of potential congestive heart failure. When the respiration data from the HF monitoring log exhibits a variation in the breathing rate/frequency that exceeds the ranges threshold, the one or more processors generate an indication of potential congestive heart failure. The indication of potential heart failure may represent an audible or vibratory output by the ICM in a manner to be detected by the patient. Additionally or alternatively, the indicatory may be a message or flag wirelessly transmitted to an external device (e.g., bedside monitor or smart phone) that then outputs an audible indication to the patient.

The operations of FIG. 5 may be performed periodically, such as to provide a day-to-day comparison of respiration data collected from the patient.

Figure 6:
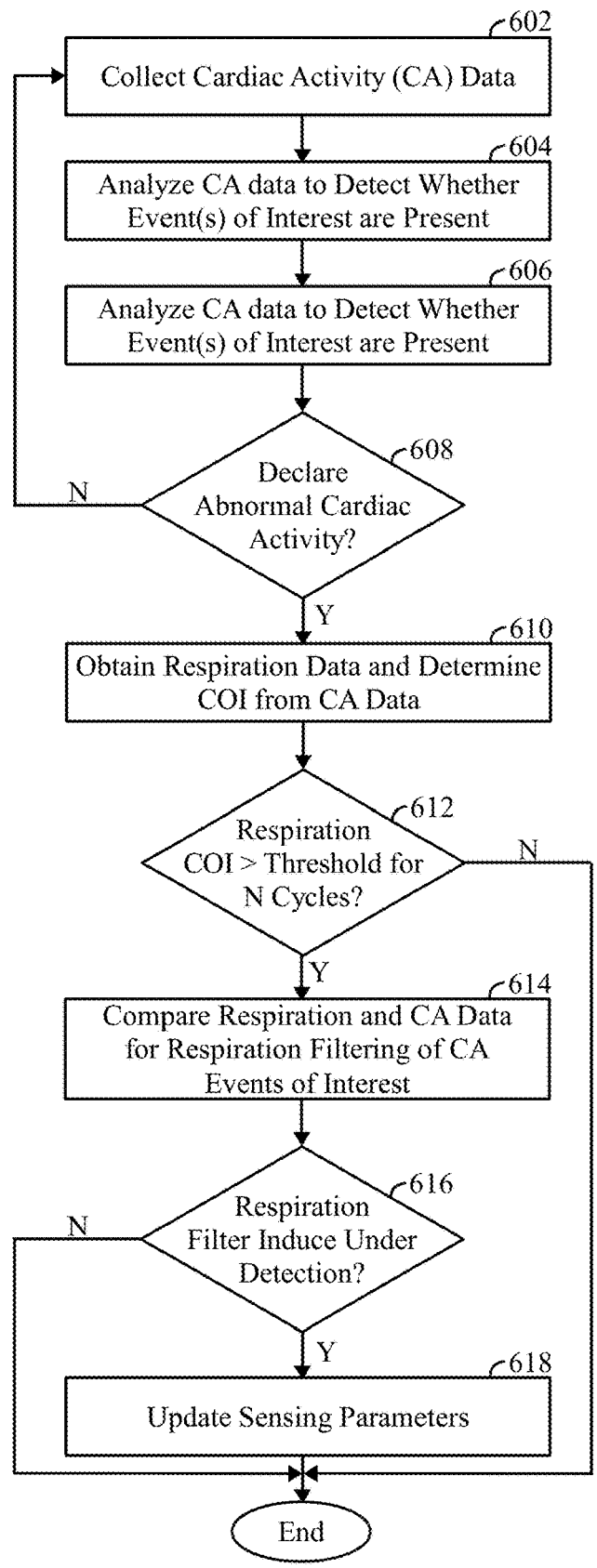
FIG. 6 illustrates a process for utilizing respiration data to reduce false detection of abnormal cardiac activity in accordance with embodiments herein.

FIG. 6 illustrates a process for utilizing respiration data to reduce false detection of abnormal cardiac activity in accordance with embodiments herein. At 602, one or more processors of the ICM collect CA data. For example, cardiac activity may be sensed at the electrodes of the ICM and processed to form digitized CA data that is stored in memory of the ICM. At 604, the one or more processors analyze the CA data to identify and label events of interest and non-event gaps. The events of interest and non-event gaps within the CA data are identified and labeled based on sensing parameters. Non-limiting examples of sensing parameters include gain, sensitivity, thresholds, decay delay, slope and overall morphology. For example, the CA data may be analyzed by a sensing circuit that has a predetermined gain and sensitivity to identify an event of interest when the signal that is sensed exceeds a threshold within a sensing window. For example, when the CA data exceeds a threshold, during a P-wave sensing window, the event of interest may be labeled as a P-wave. As another example, when the CA data exceeds a threshold, during an R-wave sensing window, the event of interest to be labeled as an R-wave. As a further example, during an R-wave sensing window, the sensing circuit may also compare the CA data to one or more predetermined slopes or morphologies to identify a QRS complex and the like. As explained hereafter, one or more of the sensing parameters may be adjusted based on the respiration data to avoid under sensing of events of interest and/or to confirm/deny non-event gaps.

As further examples, in connection with ventricular sensing, the processors may identify a first R-wave, but then not detect another R-wave within the R-R interval. Optionally, in connection with atrial sensing, the processors may identify a first P-wave, but then not detect another P-wave within the P-P interval. Optionally, the processors may identify a sensed P-wave but then not detect an R-wave within a P-R interval. As another option, the processors may not identify an R-wave, but then not detect a P-wave within a corresponding interval. When the cardiac data lacks one or more P-waves and/or R-waves, the processors may classify the cardiac cycle(s) as asystole, bradycardia or another abnormal cardiac activity.

At 608, the one or more processors determine whether a detection routine has declared a normal rhythm or abnormal cardiac activity, such as an asystole episode, a bradycardia episode and the like. When abnormal cardiac activity is not declared (e.g., the detection routine detected a normal cardiac cycle), the process returns to 602 where new CA data is collected. When abnormal cardiac activity is declared, flow continues to 610. The operations at 610 to 614 determine whether respiration activity has caused a false declaration of an abnormal cardiac activity.

At 610, the ICM obtains respiration data and determines one or more respiration COI from the respiration data. The respiration data may have been previously stored in memory at the same time as the CA data, such as by utilizing a first-in first-out loop buffer that stored a digitized output of a LPF circuit. The LPF circuit may continuously write over old respiration data in the buffer. Alternatively, the LPF circuit and buffer may only be activated periodically when it is desirable to run the process of FIG. 6. Alternatively, the respiration data may be calculated at 610 by applying a software low pass filter circuit to the CA data collected and stored at 602. The respiration COI is determined based on the respiration data in accordance with operations described herein.

At 612, the one or more processors determine whether the respiration COI exceeds (e.g., above or below) one or more corresponding thresholds for N respiration cycles, where N is 1 or more. For example, the processors may determine that peak to peak amplitude of the respiration data exceeds a threshold for 1 breath, 5 breaths, and the like. Optionally, the processors may determine whether the respiration peak to peak amplitude exceeds the threshold for a number of respiration cycles that corresponds to the number of cardiac cycles declared to exhibit abnormal CA (e.g., 3 breathes that correspond to 9 heart beats). If the respiration COI does not exceed the threshold for the desired number of respiration cycles, the process determines that respiration did not cause false detection of abnormal CA and the process ends. The ICM records the abnormal CA and does not change any other sensing parameters. Alternatively, if the respiration COI exceeds the threshold for the select number N respiration cycles, the process continues to 614.

At 614, the one or more processors compare the respiration data and CA data for respiration related filtering of CA events of interest. At 616, the one or more processors determine whether respiration filtering has induced under sensing. For example, the processors may identify respiration COI (e.g., peaks) in the respiration data and determine whether the respiration COI align, in time, with in the CA data labeled as non-event gaps. When the CA data includes non-event gaps that formed the basis for classification of a cardiac cycle and when a predetermined number of the non-event gaps align in time with the respiration COI, embodiments herein may determine that respiration filtering is causing otherwise normal CA events to be under sensed.

Returning to the example of FIGS. 2B and 2C, the process of FIG. 6 may analyze (at 608) the events 282-285 in the CA data 280. As noted above, the events 283-284 may not be sensed or classified as non-events (corresponding to the gap 294 in the markers 290). With respect to FIG. 2B, the process of FIG. 6 may determine (at 612) that the peak to peak amplitudes within the respiration data 260 exceed the corresponding threshold for a desired number of respiratory cycles. Accordingly, the process of FIG. 6 compares (at 614) the respiratory data 260 and the CA data 240, and determines that the local peaks 268, 270 correspond with sections of the cardiac data 240, for which no intrinsic event of interest was identified (e.g., non-event gaps).

Returning to FIG. 6, at 616, when the process determined that respiration filtering has not induced under sensing, the process ends. Otherwise, when the process determines that respiration filtering has induced under sensing, flow continues to 618. At 618, the one or more processors automatically update one or more sensing parameters. For example, the one or more processors may be configured to adjust the sensitivity threshold when the processor(s) identify under detection of the event of interest. With reference to FIG. 2A, the microcontroller 120 may update one or more sensing parameters of the sensing circuit 144 through the control signal 146. By way of example, the microcontroller 120 may adjust the gain, sensitivity, thresholds and other sensing parameters. The adjustments to the sensing parameters may be performed in a programmed or automatically determined manner. For example, first and second thresholds may be preprogrammed, where the sensing circuit is initially set to use a first threshold to detect a presence of events of interest. An event of interest is detected when the CA data exceeds the first threshold. No event of interest is detected when the CA data does not exceed the first threshold. At 618, the update to the sensing parameter may be to switch to the preprogrammed second (e.g., lower) threshold to be used by the sensing circuit to detect for a presence of subsequent event of interest.

Additionally or alternatively, the gain or sensitivity of the sensing circuit 144 may be automatically adjusted (e.g., increased or decreased) by predetermined increments at each iteration through 618 as the process of FIG. 6 determines that respiration filtering has induced under sensing. As another example, the sensing parameters for detecting cardiac events of interest may correspond to adjustments in a decay delay, slope or overall morphology of the CA data. At 618, the processors may adjust one or more parameters by predetermined or automatically derived amounts.

Additionally or alternatively, at 618 an output may be generated and saved to indicate that an event of interest was not correctly detected. Thereafter, a clinician, when reviewing the notification of false event detection, may adjust the sending parameters or take other corrective action.

Figure 7:
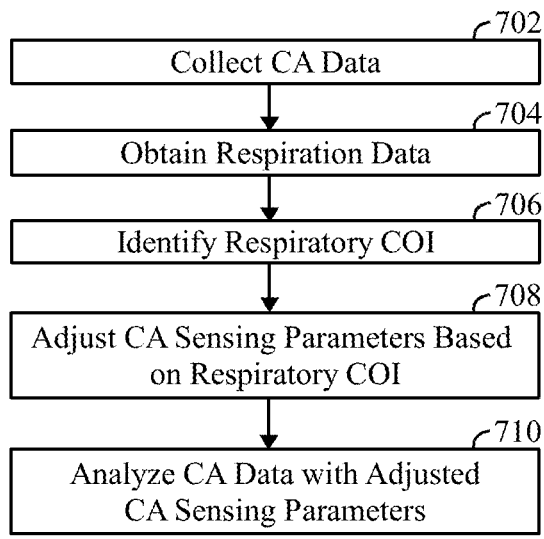
FIG. 7 illustrates a process utilizing the respiratory data to guide adjustment in the sensing parameters in real-time for the CA data in accordance with embodiments herein.

FIG. 7 illustrates a process utilizing the respiratory data to guide adjustment in the sensing parameters in real-time for the CA data in accordance with embodiments herein. At 702, one or more processors of the ICM collect CA data. At 704, one or more processors obtain respiration data from the CA data. At 706, the one or more processors determine one or more respiration COI from the respiration data.

At 708, the one or more processors adjust a CA sensing parameter based on the respiratory COI. For example, based on the point in the respiratory cycle, the processors may adjust the sensitivity of the CA sensing circuit. For example, the sensing circuit 144 (FIG. 2A) may be adjusted to increase the sensitivity as the respiratory data approaches local peaks. The sensing circuit 144 may be adjusted to decrease the sensitivity as the respiratory data approaches local valleys/minimums. Optionally, other parameters of the sensing circuit 144 may be adjusted based on the point in the respiratory cycle. Optionally, more specific types of feedback information may be derived from the respiration data in connection with determining sensing parameters. For example, the morphology, slope, frequency, phase, amplitude and other characteristics of the respiration data may be used to adjust one or more parameters for the sensing circuit 144 in connection with sensing CA data. One or more sensing parameters may be continuously updated between successive or groups of cardiac episodes based on the respiration data.

At 710, the one or more processors utilize the adjusted CA sensing parameters to analyze the CA data to identify events of interest. For example, a decreased sensitivity may be used to identify a P-wave, R-wave, ST shift, QRS complex and the like.

Figure 8:
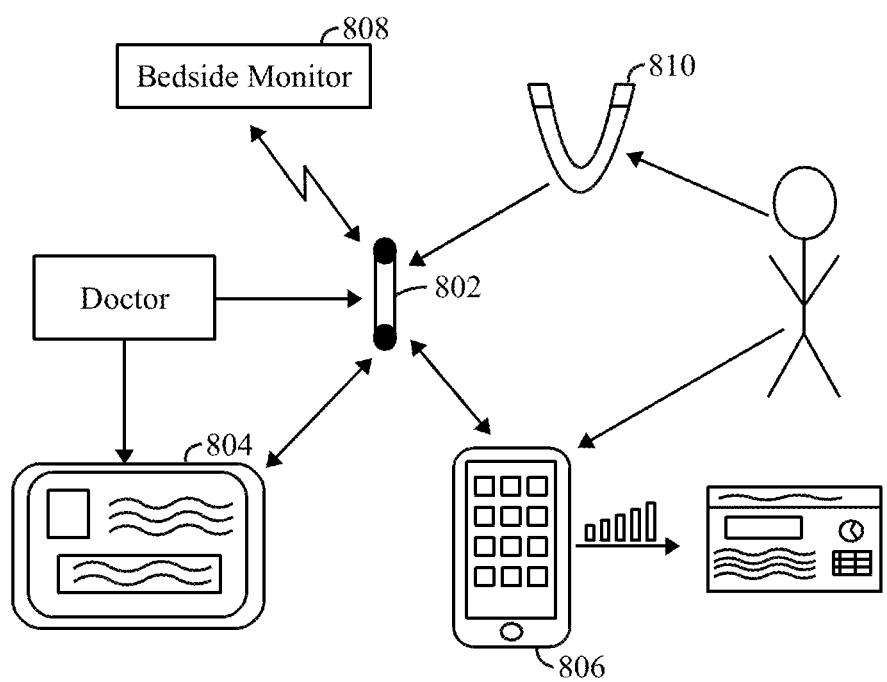
FIG. 8 illustrates a system level diagram indicating potential devices and networks in which the methods and systems herein may be utilized in accordance with embodiments herein.

FIG. 8 illustrates a system level diagram indicating potential devices and networks in which the methods and systems herein may be utilized. For example, an implantable cardiac monitoring device (ICM) 802 may be utilized to collect cardiac activity data, obtain respiratory data, and analyze the respiratory data to determine respiratory COI's and other operations in accordance with the methods and systems described herein. The ICM 802 may supply CA data, respiration data, HF monitoring log, adjustments to sensing parameters and the like, to various external and internal electronic devices, such as a tablet device 804, a smart phone 806, a bedside monitoring device 808 and the like. The devices 804-808 may perform all or portions of the processing described herein. For example, the ICM 802 may convey CA data to one or more of the devices 804-808, with the respective device 804-808 performing the remainder of the analysis described herein. Additionally or alternatively, the ICM 802 may convey the CA data and respiration data to one or more of the devices 804-808, with the respective device 804-808 performing the remainder of the analysis described herein. The devices 804-808 each include a display to display the various types of information described herein. The ICM 802 may convey the CA data, respiration data, HF monitoring log, and the like over various wireless communications links with the devices 804, 806 and 808. The ICM 802 may utilize various communications protocols and be activated in various manners. By way of example only, when a magnetic device 810 is held next to the patient, the magnetic field from the device 810 may activate the ICM 802 to transmit the cardiac activity data, respiration data, HF monitoring log, etc. to one or more of the devices 804-808.

The processes described herein for analyzing the cardiac activity data and respiration data may be implemented on the ICM 802, in which case the event data may then be wirelessly conveyed the HF monitoring log and/or any data related to detection of respiration induced under sensing to one or more of the devices 804-808. Additionally or alternatively, the devices 804-808 may also implement the processes described herein. For example, the ICM 802 may simply convey the raw cardiac activity data for an extended period of time or for discrete periods of time to one or more the devices 804-810. The devices 804-810 then analyze the raw cardiac activity data as described herein, and provide instructions back to the ICM 802, such as new sensing parameters to be implemented.

The devices 804-808 may present the respiration data, respiration COI's, changes in sensing parameters, changes in event labels and episode classifications, the HF monitoring log, etc. to clinicians in various manners.

Figure 9:
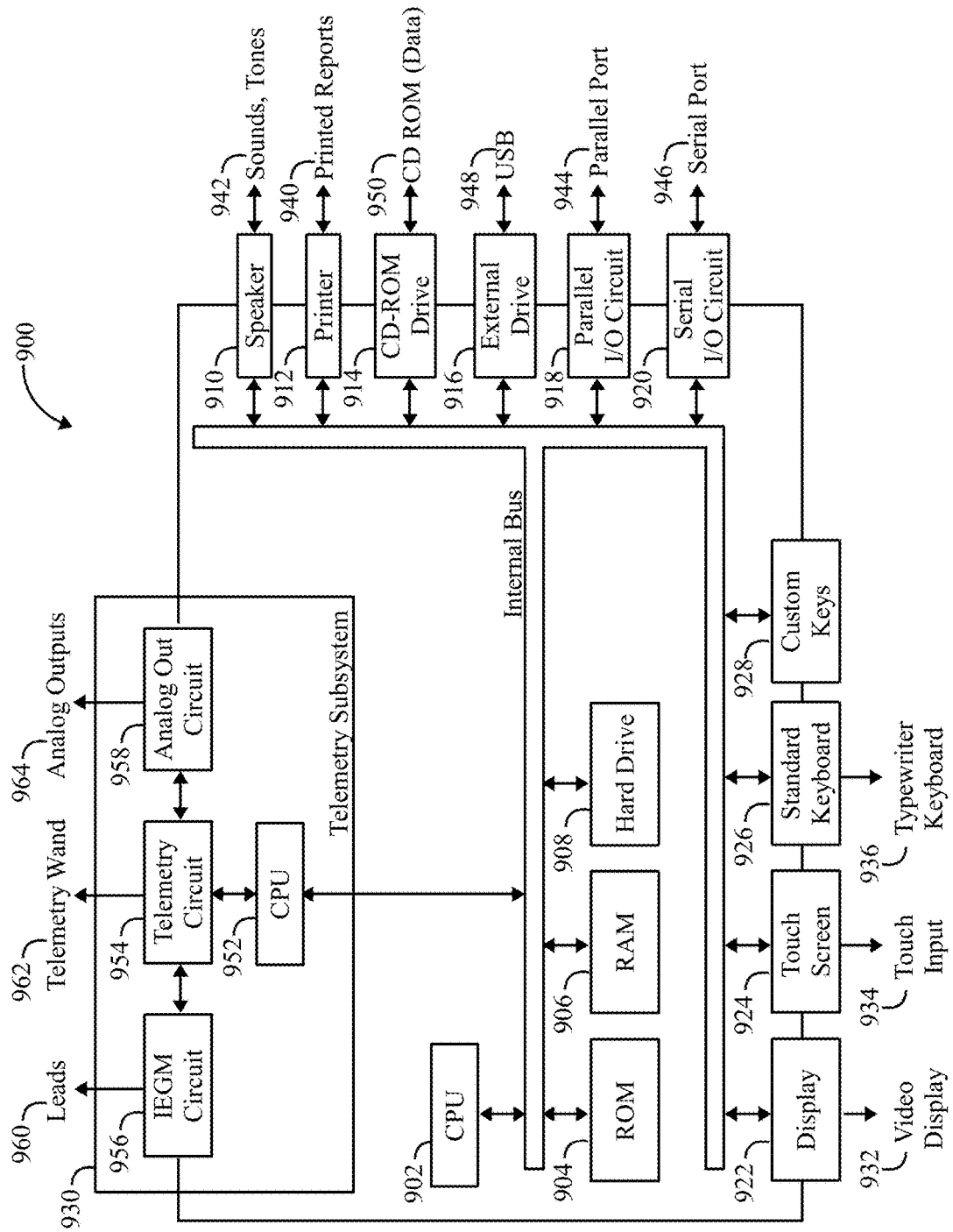
FIG. 9 illustrates a functional block diagram of the external device that is operated in accordance with the processes described herein and to interface with ICMs as described herein in accordance with embodiments herein.

FIG. 9 illustrates a functional block diagram of the external device 900 that is operated in accordance with the processes described herein and to interface with ICMs as described herein. The external device 900 may be a workstation, a portable computer, an ICM programmer, a PDA, a cell phone and the like. The external device 900 includes an internal bus that connects/interfaces with a Central Processing Unit (CPU) 902, ROM 904, RAM 906, a hard drive 908, the speaker 910, a printer 912, a CD-ROM drive 914, an external drive 916, a parallel I/O circuit 918, a serial I/O circuit 920, the display 922, a touch screen 924, a standard keyboard connection 926, custom keys 928, and a telemetry subsystem 930. The internal bus is an address/data bus that transfers information between the various components described herein. The hard drive 908 may store operational programs as well as data, such as waveform templates and detection thresholds.

The CPU 902 typically includes a microprocessor, a micro-controller, or equivalent control circuitry, designed specifically to control interfacing with the external device 900 and with the ICM or IMD. The CPU 902 performs the characteristic of interest measurement process discussed above. The CPU 902 may include RAM or ROM memory, logic and timing circuitry, state machine circuitry, and I/O circuitry to interface with the ICM or IMD. The display 922 (e.g., may be connected to the video display 932). The touch screen 924 may display graphic information relating to the ICM 900. The display 922 displays various information related to the processes described herein. For example, the display 922 may display the cardiac activity data, as well as additional information as described and illustrated herein. The display 932 (or a display on a workstation, phone, personal digital assistant, tablet device, etc.) may be configured to display an EGM with markers indicting the events labeled and classified based on the cardiac activity data.

The touch screen 924 accepts a user's touch input 934 when selections are made. The keyboard 926 (e.g., a typewriter keyboard 936) allows the user to enter data to the displayed fields, as well as interface with the telemetry subsystem 930. (for example when used in connection with a pacemaker) The printer 912 prints copies of reports 940 for a physician to review or to be placed in a patient file, and speaker 910 provides an audible warning (e.g., sounds and tones 942) to the user. The parallel I/O circuit 918 interfaces with a parallel port 944. The serial I/O circuit 920 interfaces with a serial port 946. The external drive 916 accepts an external devices 948 (e.g., USB) or other interface capable of communicating with a USB device such as a memory stick. The CD-ROM drive 914 accepts CD ROMs 950.

The telemetry subsystem 930 includes a central processing unit (CPU) 952 in electrical communication with a telemetry circuit 954, which communicates with both an EGM circuit 956 and an analog out circuit 958. The circuit 956 may be connected to terminals 960. The terminals 960 are also connected to the implantable or surface electrodes to receive and process EGM cardiac signals as discussed above. Optionally, the EGM cardiac signals sensed by the electrodes may be collected by the ICM or IMD and then transmitted, to the external device 900, wirelessly to the telemetry subsystem 930 input.

The telemetry circuit 954 may be coupled to a telemetry wand 962. The analog out circuit 958 includes communication circuits to communicate with analog outputs 964. The external device 900 may wirelessly communicate with the ICM 90 and utilize protocols, such as Bluetooth, GSM, infrared wireless LANs, HIPERLAN, 3G, satellite, as well as circuit and packet data protocols, and the like.

Figure 10:
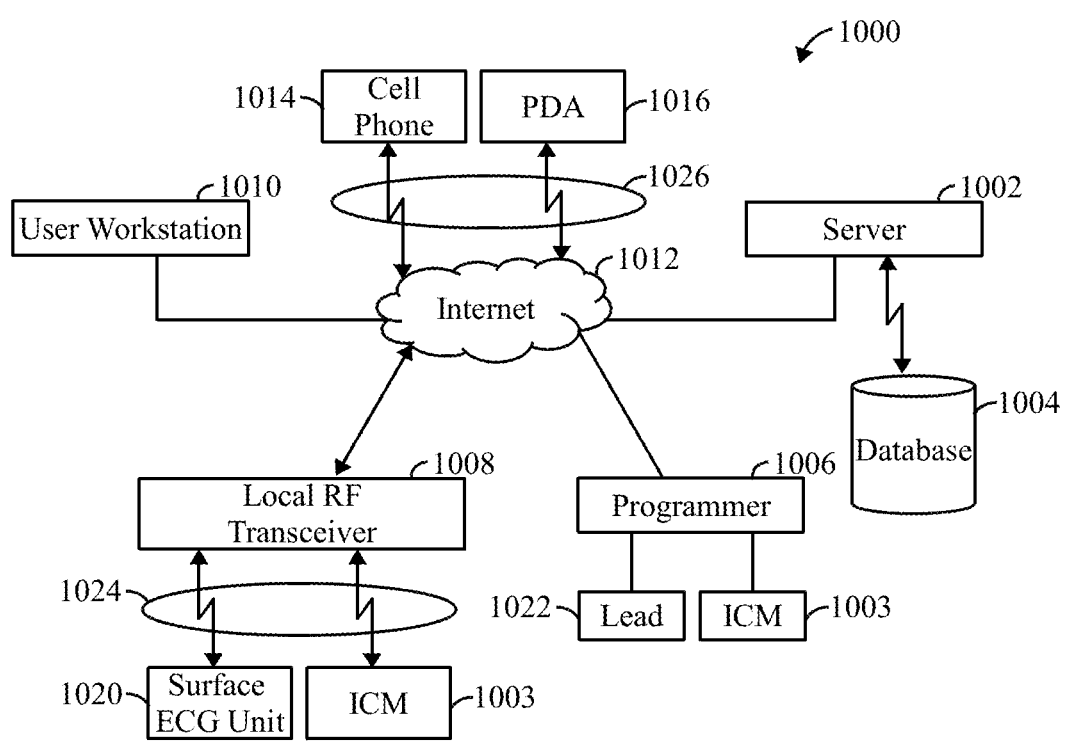
FIG. 10 illustrates a distributed processing system in accordance with one embodiment herein.

FIG. 10 illustrates a distributed processing system 1000 in accordance with one embodiment. The distributed processing system 1000 includes a server 1002 connected to a database 1004, a programmer 1006, a local RF transceiver 1008 and a user workstation 1010 electrically connected to a communication system 1012. Any of the processor-based components in FIG. 10 (e.g., workstation 1010, cell phone 1014, PDA 1016, server 1002, programmer 1006, ICM 1003) may perform the characteristic of interest measurement process discussed above.

The communication system 1012 may be the internet, a voice over IP (VoIP) gateway, a local plain old telephone service (POTS) such as a public switched telephone network (PSTN), a cellular phone based network, and the like. Alternatively, the communication system 1012 may be a local area network (LAN), a campus area network (CAN), a metropolitan area network (MAN), or a wide area network (WAM). The communication system 1012 serves to provide a network that facilitates the transfer/receipt of information such as cardiac signal waveforms, ventricular and atrial heart rates.

The server 1002 is a computer system that provides services to other computing systems over a computer network. The server 1002 controls the communication of information such as cardiac activity data, respiration data, respiration COIs, episode information, markers, cardiac signal waveforms, ventricular and atrial heart rates, and detection thresholds. The server 1002 interfaces with the communication system 1012 to transfer information between the programmer 1006, the local RF transceiver 1008, the user workstation 1010 as well as a cell phone 1014 and a personal data assistant (PDA) 1016 to the database 1004 for storage/retrieval of records of information. On the other hand, the server 1002 may upload cardiac activity data from surface ECG unit 1020 or the ICM 1003 via the local RF transceiver 1008 or the programmer 1006.

The database 1004 stores information such as cardiac activity data, respiration data, respiration COI, episode information, markers, cardiac signal waveforms, ventricular and atrial heart rates, detection thresholds, and the like, for a single or multiple patients. The information is downloaded into the database 1004 via the server 1002 or, alternatively, the information is uploaded to the server from the database 1004. The programmer 1006 is similar to the external device 900 and may reside in a patient's home, a hospital, or a physician's office. The programmer 1006 interfaces with (e.g., in connection with a pacemaker) the ICM 1003. The programmer 1006 may wirelessly communicate with the ICM 1003 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 1006 to the ICM 1003. The programmer 1006 is able to acquire cardiac signals from the surface of a person (e.g., ECGs), electrograms (e.g., EGM) signals from the ICM 1003, and/or cardiac activity data, respiration data, respiration COI, episode information, markers, cardiac signal waveforms, ventricular and atrial heart rates, and detection thresholds from the ICM 1003. The programmer 1006 interfaces with the communication system 1012, either via the internet, to upload the information acquired from the surface ECG unit 1020, or the ICM 1003 to the server 1002.

The local RF transceiver 1008 interfaces with the communication system 1012 to upload one or more of cardiac activity data, respiration data, respiration COI, episode information, markers, cardiac signal waveforms, and detection thresholds 246 (shown in FIG. 2) to the server 1002. In one embodiment, the surface ECG unit 1020 and the ICM 1003 have a bi-directional connection 1024 with the local RF transceiver 1008 via a wireless connection. The local RF transceiver 1008 is able to acquire cardiac signals from the surface of a person, cardiac activity data and other information from the ICM 1003, and/or cardiac signal waveforms, and detection thresholds from the ICM 1003. On the other hand, the local RF transceiver 1008 may download stored cardiac activity data, respiration data, respiration COI, episode information, markers, cardiac signal waveforms, and detection thresholds, and the like, from the database 1004 to the surface ECG unit 1020 or the ICM 1003.

The user workstation 1010 may interface with the communication system 1012 via the internet to download cardiac signal waveforms, ventricular and atrial heart rates, and detection thresholds via the server 1002 from the database 1004. Alternatively, the user workstation 1010 may download raw data from the surface ECG units 1020, lead 1022 or ICM 1003 via either the programmer 1006 or the local RF transceiver 1008. Once the user workstation 1010 has downloaded the cardiac signal waveforms, ventricular and atrial heart rates, or detection thresholds, the user workstation 1010 may process the information in accordance with one or more of the operations described above. The user workstation 1010 may download the information and notifications to the cell phone 1014, the PDA 1016, the local RF transceiver 1008, the programmer 1006, or to the server 1002 to be stored on the database 1004. For example, the user workstation 1010 may communicate data to the cell phone 1014 or PDA 1016 via a wireless communication link 1026.

The processes described herein in connection with analyzing cardiac activity data and respiration data may be performed by one or more of the devices illustrated in FIG. 10, including but not limited to the ICM 1003, programmer 1006, user workstation 1010, cell phone 1014, PDA 1016 and server 1002.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C # or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 102(f), unless and until such claim limitations expressly use the phrase "means for" followed by a statement of function void of further structure.

What is claimed is:

1. A computer implemented method, comprising:
under control of one or more processors, within an implantable cardiac monitor (ICM) to be implanted subcutaneously, configured with specific executable instructions,
sensing, between two or more electrodes, far field, subcutaneous electrical cardiac activity (CA) signals generated by a heart for multiple cardiac cycles, the two or more electrodes configured to be located at a site outside of a heart on or adjacent a housing of the ICM;
detecting whether an event of interest is present in the CA signals;
filtering the CA signals to obtain respiration data indicative of a respiration pattern; and
analyzing the respiration data for respiration induced under detection of the event of interest from the CA signals.

2. The method of claim 1, further comprising classifying the cardiac cycle as abnormal cardiac activity when the event of interest was not detected as present in the CA signals, the analyzing operation including confirming or denying abnormal cardiac activity based on the respiration data.

3. The method of claim 1, wherein the filtering and analyzing operations are performed when the detecting operation fails to detect the event of interest in the CA signals.

4. The method of claim 1, wherein the detecting operation detects whether the event of interest is present in the CA signals based on a sensitivity threshold, the method further comprising adjusting the sensitivity threshold based on the respiration data.

5. The method of claim 4, wherein the analyzing operation further comprises determining whether the respiration COI exceeds a threshold for a predetermined number of respiration cycles.

6. The method of claim 1, wherein the analyzing operation comprises comparing the respiration data and the CA signals for respiration induced filtering of the event of interest.

7. An implantable cardiac monitor device, comprising:
two or more electrodes provided on or adjacent a housing of the ICM, the two or more electrodes configured to be implanted at a site outside of the heart;
a CA sensing circuit configured to sense, between the two or more electrodes, far field, subcutaneous electrical cardiac activity (CA) signals generated by a heart for multiple cardiac cycles, the CA sensing circuitry configured to detect whether an event of interest is present in the CA signals;
a low pass filter (LPF) circuit configured to filter the CA signals to obtain respiration data indicative of a respiration pattern;
at least one processor; and
a memory coupled to the at least one processor, wherein the memory stores program instructions, wherein the program instructions are executable by the at least one processor to analyze the respiration data for respiration induced under detection of the event of interest from the CA signals.

8. The device of claim 7, wherein the at least one processor is configured to adjust sensing parameters of the CA sensing circuit based on the respiration data.

9. The device of claim 8, wherein the at least one processor is configured to adjust the sensing parameters by switching between first and second thresholds applied to the CA signals.

10. The device of claim 7, further comprising a physiologic sensor circuit configured to detect at least one of activity or posture data, the at least one processor configured to identify under detection of the event of interest based on the at least one of activity or posture data, wherein the CA sensing circuit detects whether the event of interest is present in the CA signals based on a sensitivity threshold, the at least one processor configured to identify under detection of the event of interest based on the respiration data, and in response thereto, adjust the sensitivity threshold.

11. A computer implemented method, comprising:
sensing, between two or more electrodes, far field, subcutaneous electrical cardiac activity (CA) signals generated by a heart for multiple cardiac cycles, the two or more electrodes provided on or adjacent a housing of an implantable cardiac monitor (ICM) to be implanted subcutaneously, the two or more electrodes configured to be located at a site outside of a heart;
under control of one or more processors configured with specific executable instructions,
a) analyzing the CA signals to determine one or more respiration characteristics of interest (COI);
b) collecting secondary data representing at least one of heart sounds, activity data, posture data or electrogram (EGM) data;
c) recording the respiration COI, information indicative of the secondary data and collection time information concerning when the electrical CA signals and secondary data were obtained; and
repeating the operations at a) to c) to form an HF monitoring log that includes a collection of respiration COI and information indicative of the secondary data over a period of time.

12. The method of claim 11, wherein the a) analyzing further comprises filtering the electrical CA signals to obtain respiration data indicative of a respiration pattern over multiple respiration cycles and analyzing the respiration data to determine the one or more respiration COI.

13. The method of claim 11, further comprising determining, as the information, a secondary index based on secondary data, the HF monitoring log including a collection of the secondary indices of the period of time.

14. The method of claim 13, further comprising analyzing at least one of the collection of respiration COI or secondary index over the period of time with respect to a baseline; and generating an indicator of potential heart failure based on a relation between the at least one of the collection of respiration COI or secondary index and the baseline.

15. The method of claim 11, further comprising providing a corrective action based on the HF monitoring log.

16. The method of claim 15, wherein the corrective action includes at least one of consulting a physician or make a change to a medication.

17. The method of claim 11, wherein the collecting the secondary data includes collecting heart sound data.

18. The method of claim 11, wherein the HF monitoring log includes information related to at least one of heart rate, heart rate variability, episode-related diagnostics, episode duration, episode count, episode date and time stamp or heart rate histogram or atrial fibrillation.

19. A system, comprising:
an implantable cardiac monitor (ICM) configured to be implanted at a site outside of the heart;
two or more electrodes provided on or adjacent a housing of the ICM, the two or more electrodes configured to be implanted at the site outside of the heart;
at least one processor; and
a memory coupled to the at least one processor, wherein the memory stores program instructions, wherein the program instructions are executable by the at least one processor to:
a) sense, between the two or more electrodes, far field, subcutaneous electrical cardiac activity (CA) signals generated by a heart for multiple cardiac cycles;

b) analyze the CA signals to determine one or more respiration characteristics of interest (COI);
c) collect secondary data representing at least one of heart sounds, activity data, posture data or electrogram (EGM) data;
d) record the respiration COI, information indicative of the secondary data and collection time information concerning when the electrical CA signals and secondary data were obtained; and
repeat the operations at a) to d) to form an HF monitoring log that includes a collection of respiration COI and information indicative of the secondary data over a period of time.

20. The system of claim 19, wherein the processor is further configured to analyze the CA signals by filtering the electrical CA signals to obtain respiration data indicative of a respiration pattern; and analyze the respiration data to determine the one or more respiration COI.

21. The system of claim 19, wherein the processor is further configured to determine, as the information, a secondary index based on secondary data, the HF monitoring log including a collection of the secondary indices of the period of time.

22. The system of claim 19, wherein the ICM includes a housing that encloses the memory and the at least one processor, the ICM including a transceiver to wirelessly transmit the HF monitoring log to an external device.

23. The system of claim 19, wherein the HF monitoring log includes information related to at least one of heart rate, heart rate variability, episode-related diagnostics, episode duration, episode count, episode date and time stamp or heart rate histogram or atrial fibrillation.

24. The system of claim 19, wherein further comprising an external device that houses at least a portion of the memory and an external processor from the at least one processor, the ICM including a transceiver to wirelessly transmit the CA signals to the external device, the external device configured to implement the analyze and record operations to form the HF monitoring log.

25. The system of claim 24, wherein the external device is further configured to collect the secondary data, separate from the ICM, and record the information indicative of the secondary data.

* * * * *